(12) United States Patent  
Kitaguchi et al.

(10) Patent No.: US 6,333,962 B1
(45) Date of Patent: Dec. 25, 2001

(54) NON-DESTRUCTIVE INSPECTION APPARATUS AND INSPECTION SYSTEM USING IT

(75) Inventors: Hiroshi Kitaguchi, Naka; Shigeru Izumi, Tokyo; Hiroshi Miyai, Hitachi; Katsutoshi Sato, Hitachi; Yasuko Aoki, Hitachi; Yukiya Hattori, Hitachi, all of (JP)

(73) Assignee: Hitachi, Ltd., Tokyo (JP)

( * ) Notice: Subject to any disclaimer, the term of this patent is extended or adjusted under 35 U.S.C. 154(b) by 0 days.

(21) Appl. No.: 09/326,598

(22) Filed: Jun. 7, 1999

Related U.S. Application Data

(62) Division of application No. 08/832,163, filed on Apr. 2, 1997, now Pat. No. 5,933,473.

(30) Foreign Application Priority Data

| Apr. 4, 1996 | (JP) | 8-82330 |
| Dec. 13, 1996 | (JP) | 8-333344 |
| Jan. 8, 1997 | (JP) | 9-1136 |
| Mar. 3, 1997 | (JP) | 9-47571 |

(51) Int. Cl.$^7$ .................................................. G01T 1/00
(52) U.S. Cl. ........................ 378/57; 378/146; 378/149
(58) Field of Search .................... 378/57, 98.8, 146, 378/147, 154, 155, 149; 250/370.09

(56) References Cited

U.S. PATENT DOCUMENTS

| 4,041,315 | 8/1977 | Hounsfield . | |
| 4,389,729 | 6/1983 | Stein . | |
| 4,411,012 | * 10/1983 | Pfeiler et al. | 378/17 |
| 4,493,098 | 1/1985 | Riihimaki et al. . | |
| 4,495,636 | 1/1985 | Jacobs et al. . | |
| 4,709,382 | * 11/1987 | Sone | 378/62 |
| 4,933,961 | 6/1990 | Rushbrooke et al. . | |
| 5,070,519 | * 12/1991 | Stein et al. | 378/146 |
| 5,259,016 | 11/1993 | Dickerson et al. . | |
| 5,463,224 | 10/1995 | Burstein et al. . | |
| 5,550,378 | 8/1996 | Skillicorn et al. . | |
| 5,644,612 | 7/1997 | Moorman et al. . | |
| 5,805,662 | * 9/1998 | Kurbatov et al. | 378/87 |
| 5,933,473 | * 8/1999 | Kitaguchi et al. | 378/57 |

FOREIGN PATENT DOCUMENTS

| 2 082 873 | 3/1982 | (GB) . |
| 58-58451 | 4/1983 | (JP) . |
| 59-181133 | 10/1984 | (JP) . |
| 61-254837 | 11/1986 | (JP) . |
| 63-167248 | 7/1988 | (JP) . |
| 3-48188 | 3/1991 | (JP) . |
| 5-302997 | 11/1993 | (JP) . |
| 6-201835 | 7/1994 | (JP) . |
| 6-269439 | 9/1994 | (JP) . |
| WO 9 010 859 | 9/1990 | (WO) . |

* cited by examiner

Primary Examiner—David P. Porta
(74) Attorney, Agent, or Firm—Antonelli, Terry, Stout & Kraus, LLP

(57) ABSTRACT

A non-destructive inspection apparatus has a radiation source, a radiation detector, a radiation source diver, a detector driver, a drive controller, a delay circuit, a radiation signal processing circuit, a memory, a computer, a display device, and an input device. The radiation detector consists of one-dimensional or two-dimensional array of detectors having a long collimator whose pores are in parallel with the radiation angle of the radiation emitted in an angular pattern from the radiation source, whereby a transmission image of a large size structure can be obtained at high speed and with a high resolution. Furthermore, the detect position in an inspection object can be specified by analyzing a plurality of specified transmission images using the inspection apparatus.

4 Claims, 35 Drawing Sheets

SECTIONAL VIEW

AFTER ALIGNMENT

BEFORE ALIGNMENT

FIG. 43a X-RAY PULSE
FIG. 43b OUTPUT VOLT. OF DETECTOR
FIG. 43c INPUT OF DELAY CIRCUIT
FIG. 43d OUTPUT OF DELAY CIRCUIT (SAMPLE HOLDING PULSE)

FIG. 53a TRIGGER SIG.

FIG. 53b X-RAY PULSE

NON-DESTRUCTIVE INSPECTION APPARATUS AND INSPECTION SYSTEM USING IT

CROSS REFERENCE TO RELATED APPLICATION

This is a divisional of U.S. application Ser. No. 08/832,163, filed Apr. 2, 1997, now U.S. Pat. No. 5,933,473, issued Aug. 3, 1999, the subject matter of which is incorporated by reference herein.

BACKGROUND OF THE INVENTION

The present invention relates to a non-destructive inspection apparatus for inspecting large objects at high speed with a high precision, and an inspection system using such an apparatus.

An X-ray inspection apparatus, which is a kind of apparatus widely used as a non-destructive inspection apparatus, is shown in FIGS. 1a and 1b. The example shown in FIG. 1a uses a direct radiographic method of irradiating X-rays 121 generated from an X-ray source 120 onto an object 122 and picking up images on X-ray films 124 installed on the back side of the object 122. On the other hand, an example of an apparatus using no X-ray films, as indicated in JP-A-61-254837 and JP-A-58-58451, uses an indirect radiographic method in which light is emitted from a fluorescent screen 105 arranged on the back side of the object 122 in response to X-rays emitted from the X-ray source 120, as shown in FIG. 1b. The light is then amplified using an image intensifier 112, and light images are picked up by a camera 107. In these methods, a two-dimensional radiation inspection process can be carried out.

To improve the sensitivity of a conventional apparatus, it is necessary to make the fluorescent screen and image intensifier thicker to increase the sensitivity of the fluorescent screen. However, there is a problem in that these methods produce a poor resolution (the image becomes blurred).

SUMMARY OF THE INVENTION

In the X-ray inspection apparatus described in the above conventional example, radiography of an object of large size with a high sensitivity is not taken into account, even though improvement in the sensitivity is indispensable if the radiography is to be performed in a short time. Therefore, an object of the present invention is to solve the aforementioned problems and to provide a high-energy non-destructive inspection apparatus for imaging a large building or similar large object at high speed with high precision, and to provide an inspection system using such an apparatus.

To image a large object, such as a building, with high precision, it is desirable to employ a radiation generator (an accelerator, etc.), a two-dimensional collimator having a plurality of pores or channels arranged not in parallel with each other, but arranged so as to be in parallel with the radiation angle of radiation spreading with a solid angle (cone-shaped radiation) emitted from the radiation generation source, and a plurality of radiation detection elements (scintillators) for detecting the radiation entering the plurality of pores or channels arranged in parallel with the radiation angle and to provide an optical means for directly focusing the radiation as pixels.

BRIEF DESCRIPTION OF THE DRAWINGS

FIG. 4b is a diagram of the sections A—A and B—B in FIG. 4a.

DETAILED DESCRIPTION OF THE EMBODIMENTS

Figure 2:
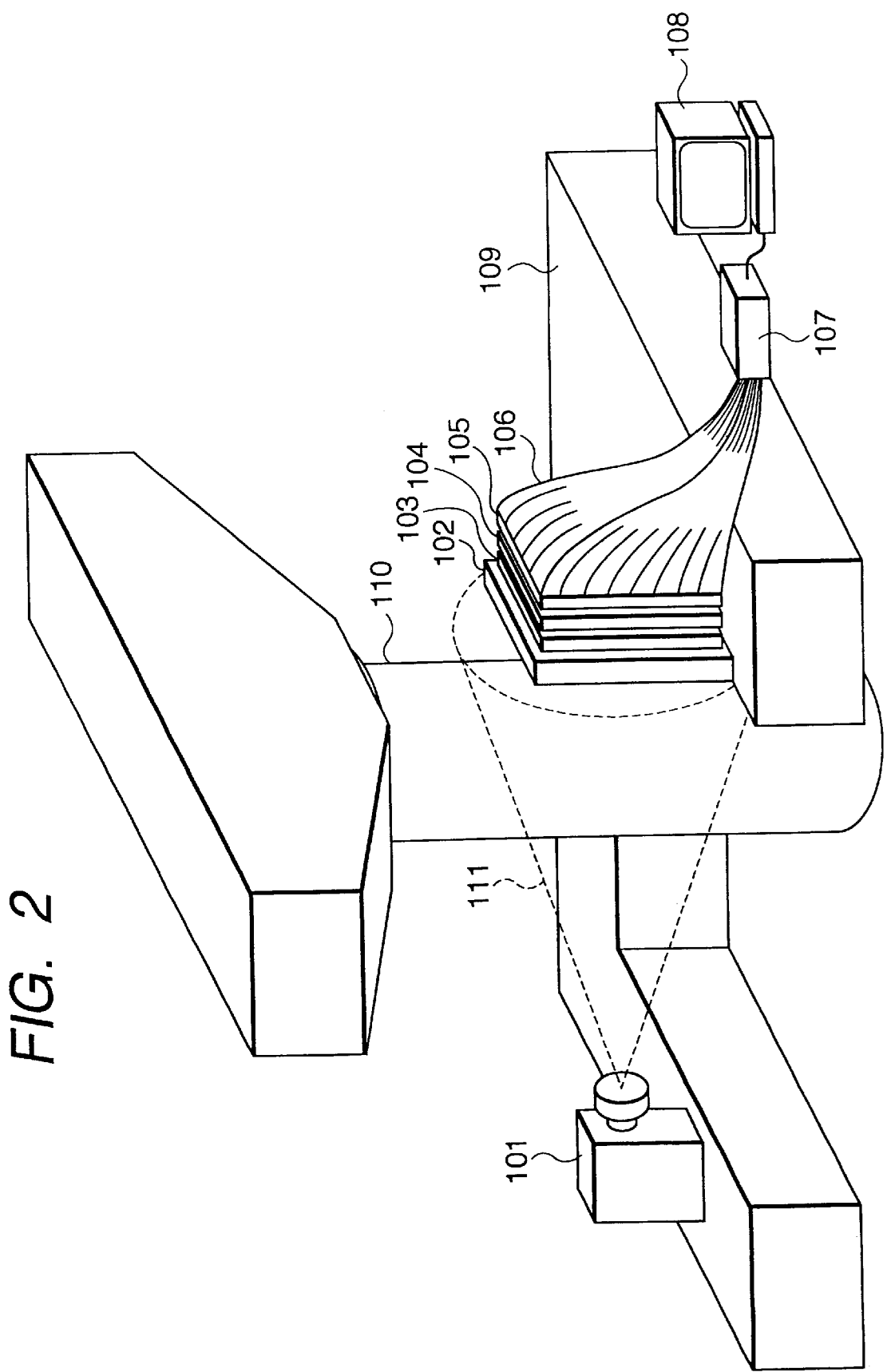
FIG. 2 is a perspective view showing the constitution of a high-energy radiation inspection apparatus which is an embodiment of the present invention.

Various embodiments of the present invention will be described in detail hereunder with reference to the accompanying drawings. FIG. 2 shows an embodiment of a high-energy non-destructive inspection apparatus according to the present invention. High energy X-rays 111 (1 MeV or more) generated by an accelerator 101 are irradiated onto an inspection object (for example, heavy concrete with a density of 1 g/cm$^3$ or more, an imaging area of 1 m$^2$ or more, and an X-ray transmission thickness of 1 m or more), such as a pier of an expressway.

In the following description of this embodiment, examples in which X-rays are used as inspection radiation will be referred to. However, the present invention is not limited to the use of X-rays, but radiation generally used in this field, for example, gamma rays or neutrons, may be used as well. In this embodiment, X-rays are radiated from an X-ray source in a cone shape with a solid angle. However, when necessary, X-rays also may be radiated in a fan shape, which represents one cross section shape of a cone.

A pre-collimator (not shown in the drawing) is provided as a target of the accelerator 101 for generating X-rays and the cone beam 111 (X-rays in a cone shape) is radiated onto the inspection object 110. On the back side of the inspection object 110, a radiation detection means comprising a two-dimensional collimator 102 having pores or channels which are individually arranged in parallel with the cone beam angle of the accelerator 101 is provided. The radiation detection means is a detection means for detecting and converting X-rays to light, which comprises a collimator for suppressing scattered light of the cone-shaped radiation and mainly detecting direct radiation, and a scintillator (an MCP (micro-channel plate), a fluorescent screen, etc.) for converting X-rays emitted from the collimator to light.

A plurality of pores or channels are formed in the collimator 102, and a plurality of longitudinal scintillators are arranged in the length direction of the pores and in parallel with X-rays passing through the plurality of pores, or a scintillator 103 is provided in the latter stage of the collimator. The longitudinal scintillators are arranged along the direction of direct radiation of the cone beam of the X-ray source, so that they have sensitivity only in the incident direction of the radiation. By doing this, a directional and highly sensitive radiation detection which suppresses an effect of scattered X-rays is made possible. The highly sensitive radiation detection allows radiography at a low dose rate and shortens the exposure time remarkably. As the pore diameter of the collimator 102 decreases and each pitch also decreases, radiography at a high resolution is made possible.

Needless to say, as the pore diameter decreases further, the number of radiation detection systems increases. When an imaging area of 1 m$^2$ is exposed by a collimator with pores having a diameter of 1.0 mm, at least 10$^5$ detection systems are required. It is possible to optically connect an optical fiber 106 which can directly focus scintillation light onto the scintillation detector 103 and to produce images of a large structure with a large area at low cost by use of space transmission of light.

A micro-channel plate (MCP) 104 and a fluorescent screen 105 are optically connected to the latter stage of the scintillation detector 103 so as to amplify light. An X-ray transmission image of the inspection object 110 which is made luminous by the fluorescent screen 105 is transmitted by an optical fiber bundle 113 (a bundle of a plurality of optical fibers 106) and imaged by an imaging camera 107. This image is inspected and diagnosed for the presence of a defect and to determine the degree of corrosion in the inspection object 105 by image processing performed by an arithmetic display unit 108. The components from the accelerator 101 to the connection portion of the fluorescent screen 105 and the optical fibers 106 are installed on a stage 109, which is moved along the imaging portion of the inspection object 110 by a drive mechanism (not shown in the drawing).

Figure 1A:
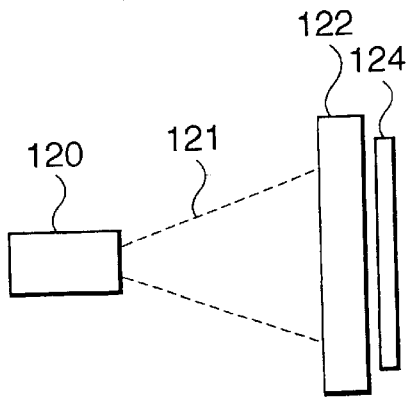
FIGS. 1a and 1b are diagrams showing different forms of a conventional X-ray inspection apparatus.
Figure 1B:
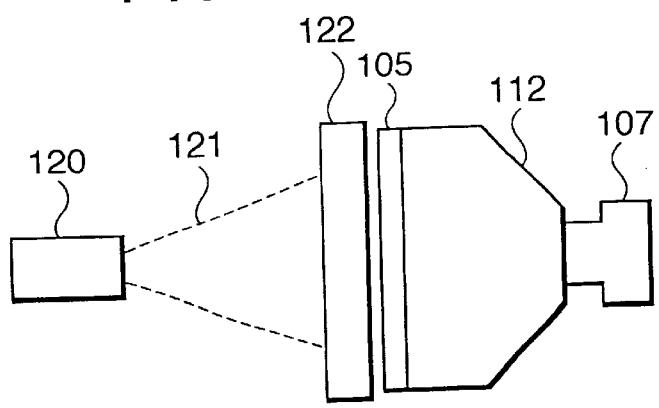
Figure 3:
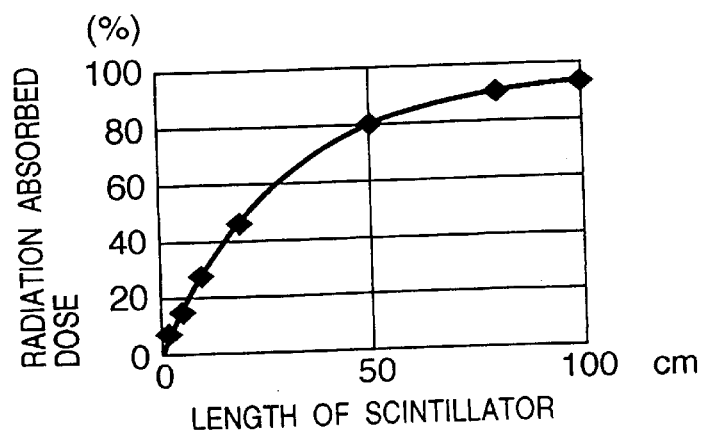
FIG. 3 is a graph showing the relation between the scintillator length and an X-ray absorbed dose.

With respect to the length of the longitudinal scintillator, as it gets longer, the sensitivity improves resultantly. From the view point of a large structure and a reduction in the radiation absorption coefficient, it is desirable that the length of the scintillator is about 5 to 50 cm in practical use. This can be explained by the graph in FIG. 3 wherein the horizontal axis represents the length of the scintillator and a vertical axis represents the radiation absorbed dose at 1 MeV of X-rays. A radiation absorbed dose of 10 to 90% is practically used and the corresponding length of the scintillator is about 5 to 90 cm. However, a length of 5 to 50 cm is most desirable because the radiation absorbed dose increases remarkably in this length range.

An X-ray detector using a general purpose X-ray film and the apparatus of the present invention will be compared with respect to sensitivity.

(1) Assuming that the sensitivity of the X-ray film per unit volume is the same as that of the scintillator, the thickness of the X-ray film or the length of the scintillator results in a sensitivity difference. If the thickness of the conventional X-ray film is set to about 100 $\mu$m and the length of the scintillator of the present invention is set to 20 cm, the sensitivity will increase about 2000 times.

(2) To recognize an X-ray image on an X-ray film, an X-ray density of $10^4$ (X-rays/mm$^2$) and an area of $10^{-2}$ mm$^2$ or more are required. Namely, an image can be picked up by incidence of 100 X-rays per $10^{-2}$ mm$^2$. On the other hand, when a scintillator is used, if one X-ray enters an area of $10^{-2}$ mm$^2$, which is the same as that of the X-ray film, an image can be picked up. As a result, the sensitivity when the scintillator is used is about 100 times of that when the X-ray film is used.

(3) When a two-dimensional collimator is arranged according to the present invention, the sensitivity becomes 10 times that when no collimator is used.

(4) On the other hand, due to light transmission loss caused by use of the optical fiber bundle for information transmission, the sensitivity of the present invention is reduced to 1/10 times the sensitivity of a conventional apparatus.

When the sensitivities obtained by the items (1) to (4) mentioned above are multiplied by each other, the product becomes about $2\times10^5$ times, which is similar to the aforementioned value of about $10^5$ times. This makes it possible to shorten the inspection time substantially and moderate the problem of the radiation controlled area setting remarkably. By doing this, a radiation detection device of high speed and high sensitivity can be provided.

Figure 4A:
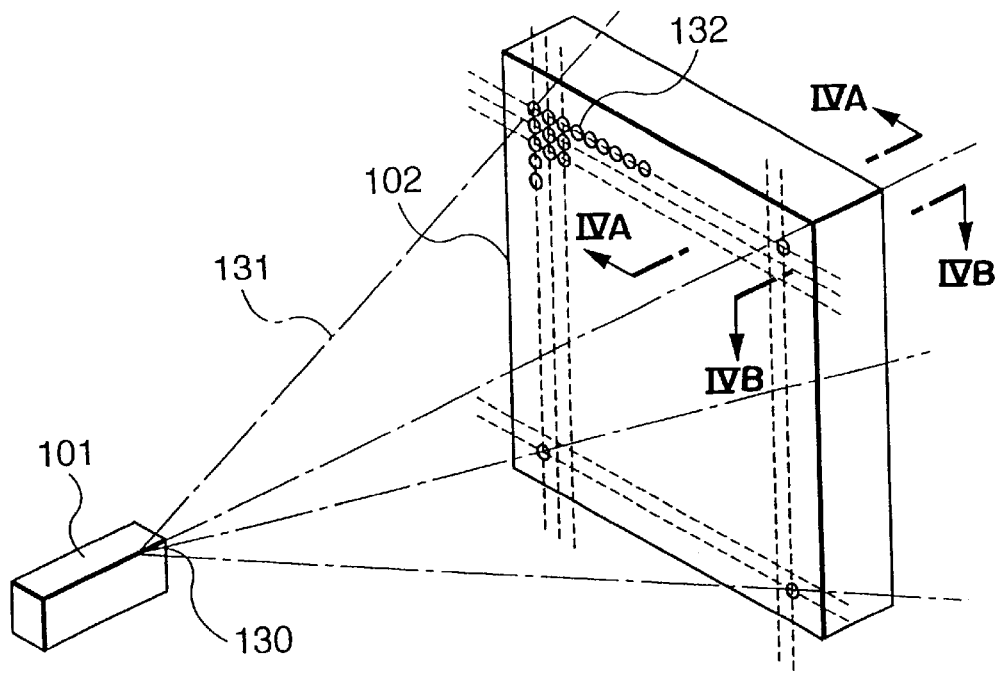
FIG. 4a is a diagram showing the appearance of the collimator in the aforementioned embodiment.
Figure 4B:
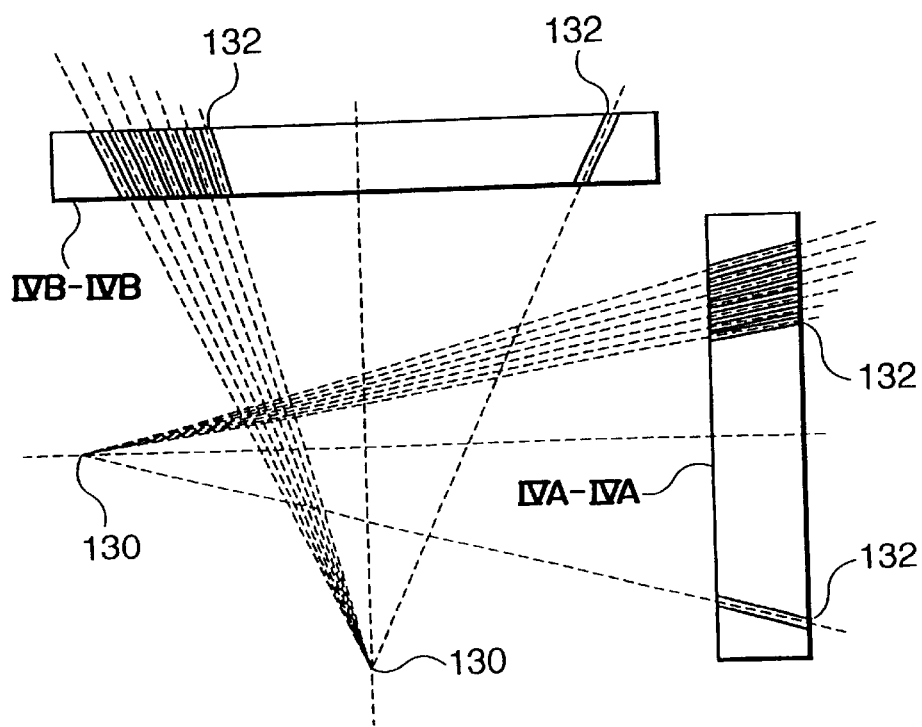

FIG. 4a shows details of the collimator. Pores 132 of the collimator 102 are provided two-dimensionally and extend in parallel with the radiation angle of a cone beam 131 emitted from an X-ray generation point 130 (focus) of the accelerator 101. FIG. 4b shows the sections B—B and A—A shown in FIG. 4a. The collimator 102 suppresses the incidence of the scattered X-rays generated from the inspection object and allows only directly transmitted radiation of the cone beam 131 to reach the scintillator (not shown in the drawing) provided on the latter stage.

Figure 5:
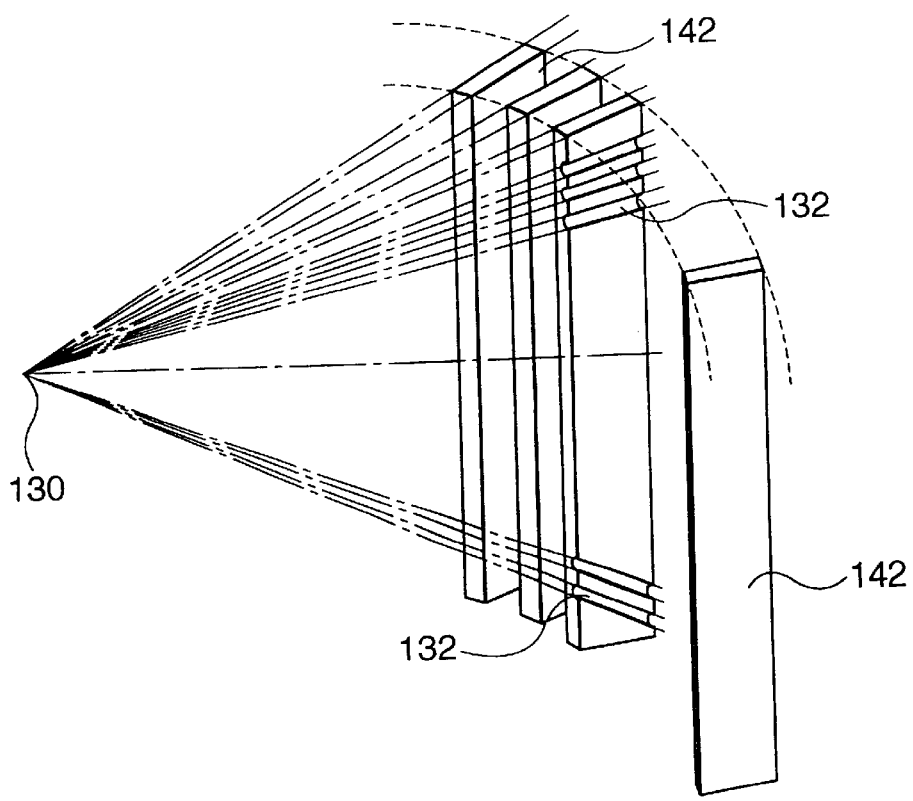
FIG. 5 is a diagram showing a partial structure of the collimator.

FIG. 5 shows one form of the structure of the collimator. A plurality of collimator plates 142 arranged along the radiation angle of the cone beam which is determined by the X-ray generation point 130 (focus) and the setting position of the collimator are laminated. A plurality of collimator pores 132 (notch) extending along with the angle of the cone beam are formed in each collimator plate 142. Since the collimator plates 142 are laminated, a two-dimensional array collimator transmitting the direct radiation of the cone beam can be produced easily. As a collimator material for suppressing scattered X-rays, for example, a material having a high density, such as tungsten, lead, and SUS (stainless steel), is preferred.

Figure 6:
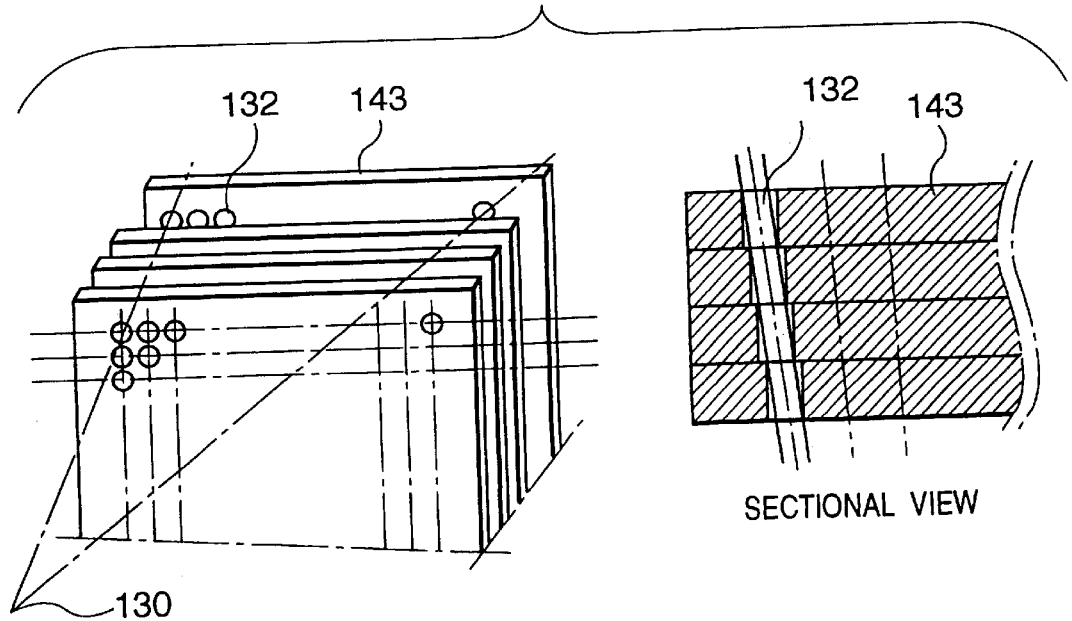
FIG. 6 is a diagram showing a partial structure of the collimator.

FIG. 6 shows an example of a different collimator structure from that shown in FIG. 5. In this example, collimator plates 143 are arranged perpendicularly to the incident plane of the cone beam. A pore 132 along the angle 40 of the cone beam is made in each collimator plate 143. This example shows a structure capable of easy production compared with the structure shown in FIG. 5. Needless to say, a two-dimensional pore along the angle of the cone beam can be produced in a collimator plate by machining, though it depends on the pore length.

In addition, although not shown in the drawing, a curved collimator in which the curvature is set so that the distance from the radiation source to the collimator becomes an equal distance can be produced. Since the distance from the radiation source to the collimator is fixed, the radiation is decreased in attenuation and can be measured precisely.

Figure 7:
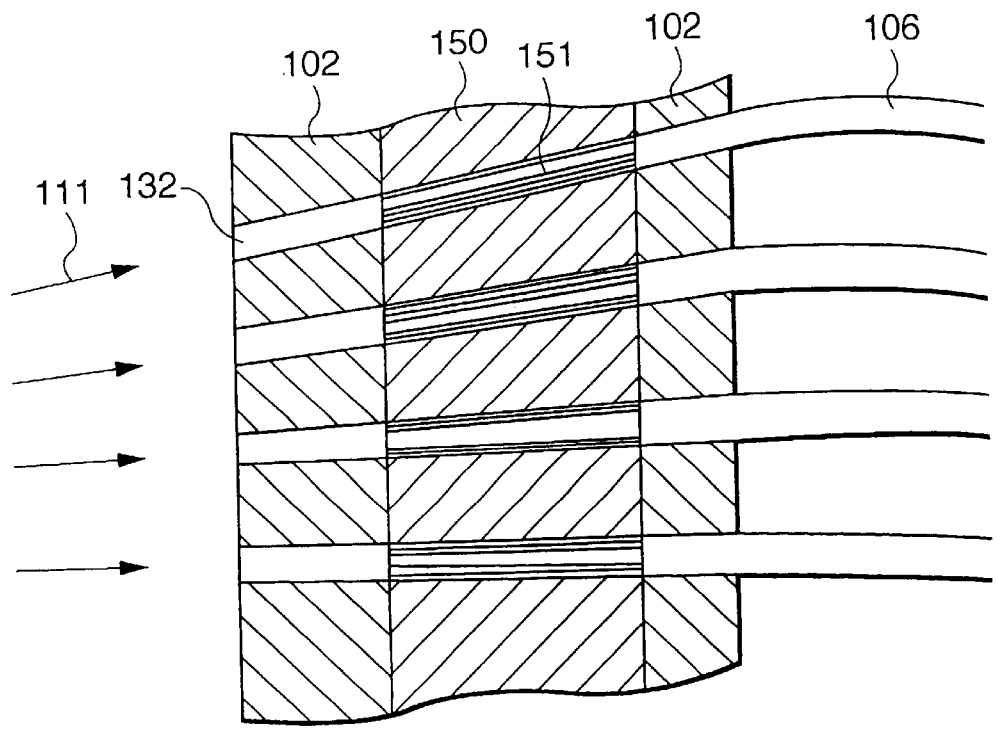
FIG. 7 is a partial sectional view showing a structure of the detection unit of the aforementioned embodiment.

FIG. 7 shows the structure of the detection unit of the present invention. On the back side of the collimator 102 opposite the cone beam 111, a scintillator case 150 (made of a material equivalent to that of the collimator, such as lead, SUS, or tungsten) holding a scintillator 151 along the angle of the radiation is provided and the optical fibers 106 for light transmission are connected to the latter stage thereof. A scintillator 151 is arranged in each of the plurality of pores of the collimator 102 and it is an important design condition to arrange the scintillators 151 so that they coincide with the radiation angle of the cone beam. By doing this, when X-rays enter in the longitudinal direction of the scintillators 151, the direct radiation component of the cone beam can be detected efficiently.

Furthermore, the arrangement shown in FIG. 7 is comparable with a case wherein an X-ray film which is sufficiently thick to detect radiation is arranged in place of the scintillator case 150 and the scintillators 151. When an X-ray film is provided, the cone beam 111 entering the collimator pores 132 will expose the parts of the X-ray film corresponding to the size of the pores. However, the region of the X-ray film, other than the parts equivalent to the size of the pores, also will be exposed to light by the scattering effect of radiation after the cone beam ill is irradiated to the X-ray film, so that the image becomes blurred.

On the other hand, when the arrangement of the present invention as shown in FIG. 7 is used, even if scattered light is included in the X-rays emanating from the pore of each collimator at a corresponding scintillator 151, scattered light reaching an adjacent scintillator from the pore is shielded by the scintillator case 150, and so scattered light generated in the scintillator 151 does not affect the neighboring scintillators due to this shielding by the scintillator case 150. Therefore, the influence of the scattering effect can be minimized, the image does not become blurred, and radiation can be detected more accurately. Therefore, according to the present invention in which a scintillator is provided for each pore of a collimator, images do not become blurred and the radiation can be detected with high precision.

As a scintillator material, bismuthgermarate ($Bi_4Ge_3O_{12}$), cadmium tung-state ($CdWO_4$), or a plastic scintillator can be used according to the required sensitivity. Using this constitution, highly directional and highly sensitive detection can be realized easily. High sensitivity due to the aforementioned detection structure enables inspection at a low dose rate of about 1/100000 of that of the conventional method. In the aforementioned detector structure, the collimator 102 and the scintillator case 150 are separately provided. However, it goes without saying that a structure in which the scintillators 151 are inserted into the pores of the collimator 102 provides a more simple structure.

Figure 8:
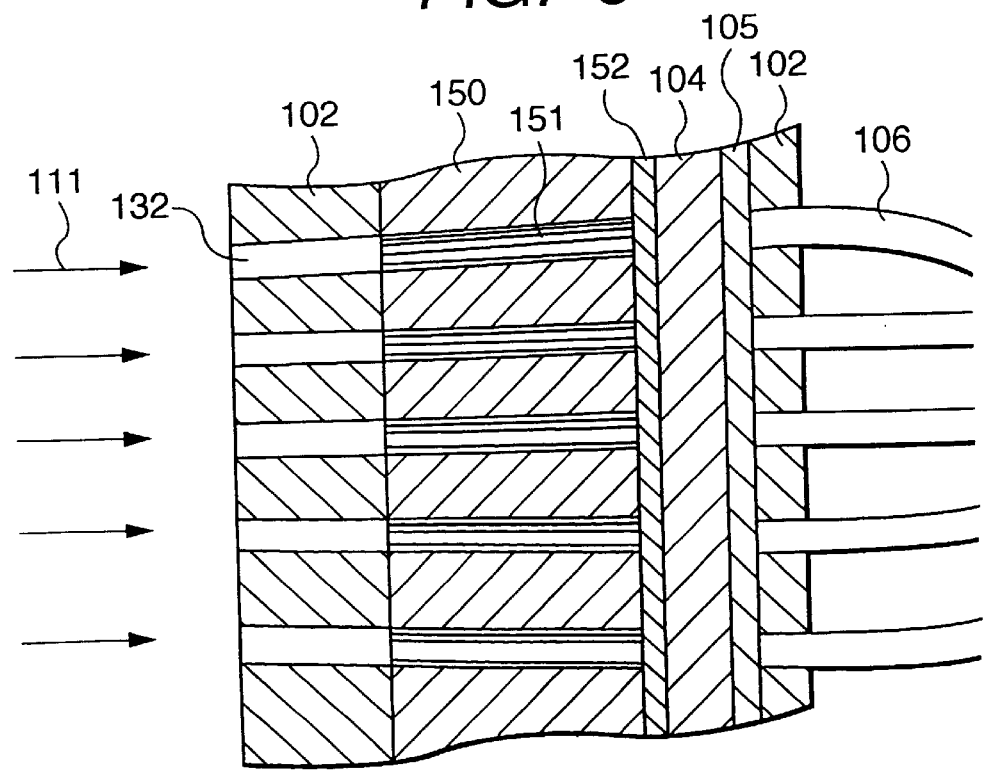
FIG. 8 is a partial sectional view showing another example of a structure of the detection unit of the aforementioned embodiment.

FIG. 8 shows an example of the detector unit of the present invention. When the quantity of the scintillation light detected by the scintillators 151 is insufficient in the transmission of light to the latter stage by the optical fibers 106, micro-channel plates (MCP) 104 are provided between the scintillators 151 and the optical fibers 106 so as to amplify the light. In this example, long-distance transmission by the optical fibers is made possible and an inspection system can be constructed flexibly.

Figure 9:
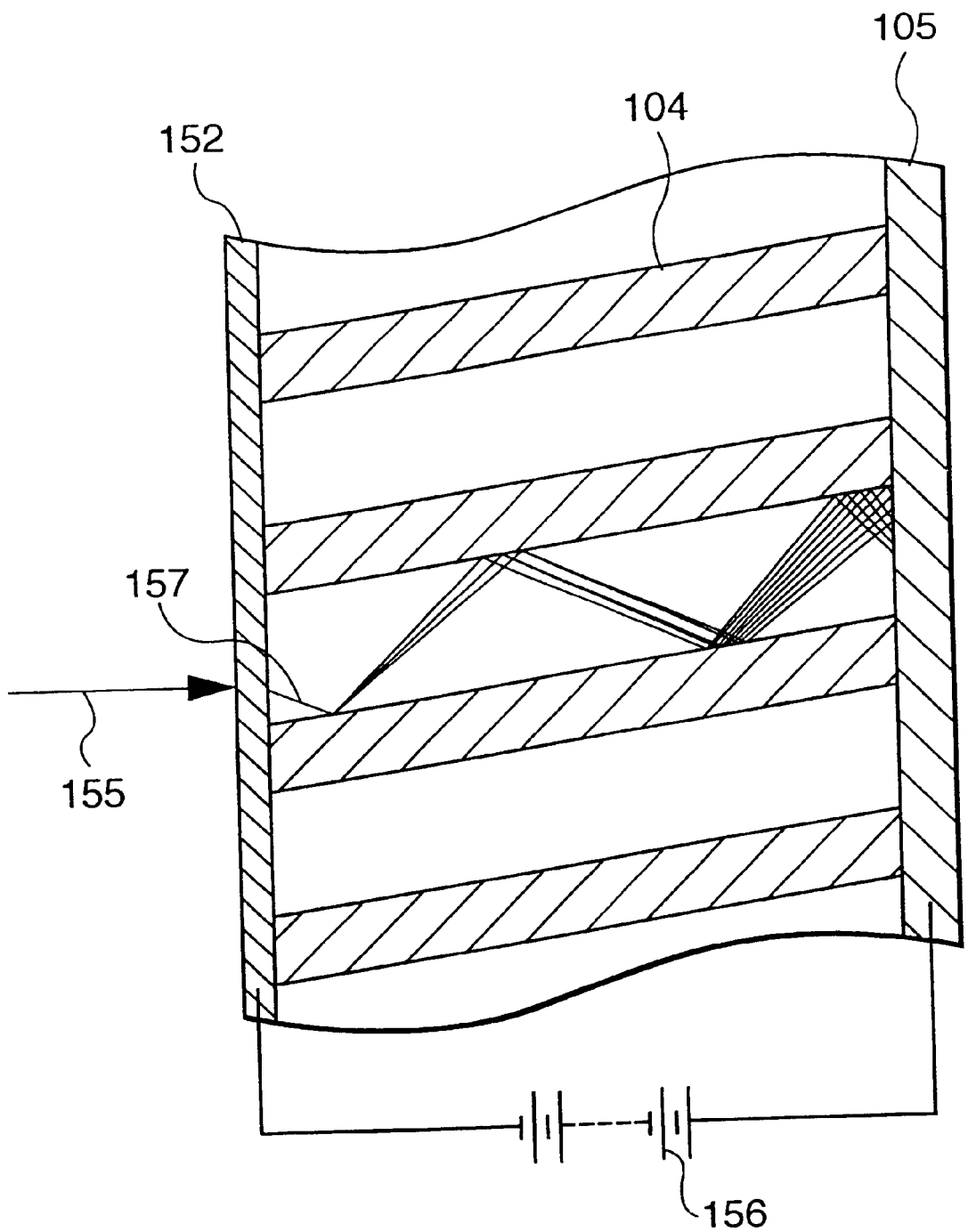
FIG. 9 is a partial sectional view showing a schematic structure of the micro-channel plate (MCP) of the aforementioned embodiment and the principle thereof.

FIG. 9 shows the principle of the micro-channel plates. The MCPs are of a plate structure having many through holes with a material serving as a resistor and a secondary electron emitter provided as an inner wall. A scintillation light beam 155 enters a photo electric surface 152 and generates electrons 157. A high voltage power supply 156 of about 1000 V is connected to the ends of the through holes and an electric field is generated inside the through holes by application of the voltage. Electrons are accelerated by the electric field inside the through holes and reach the inner walls of the through holes. If electrons have a sufficient speed at this time, a plurality of secondary electrons are generated. Secondary electrons are accelerated by the electric field inside the through holes and collide with the inner walls of the through holes once again.

In this case, the applied voltage is adjusted so that secondary electrons reach a sufficient speed to emit a plurality of secondary electrons. This process is repeated and electrons are amplified. In a general MCP, the gain of electrons is about 1000. When several laminal structures like this are laminated, the gain of electrons can be increased. Amplified electrons collide with the fluorescent screen 105 installed in the neighborhood of the outlets of the through holes and amplified fluorescence can be obtained. In this way, the scintillation light can be amplified easily.

Figure 10:
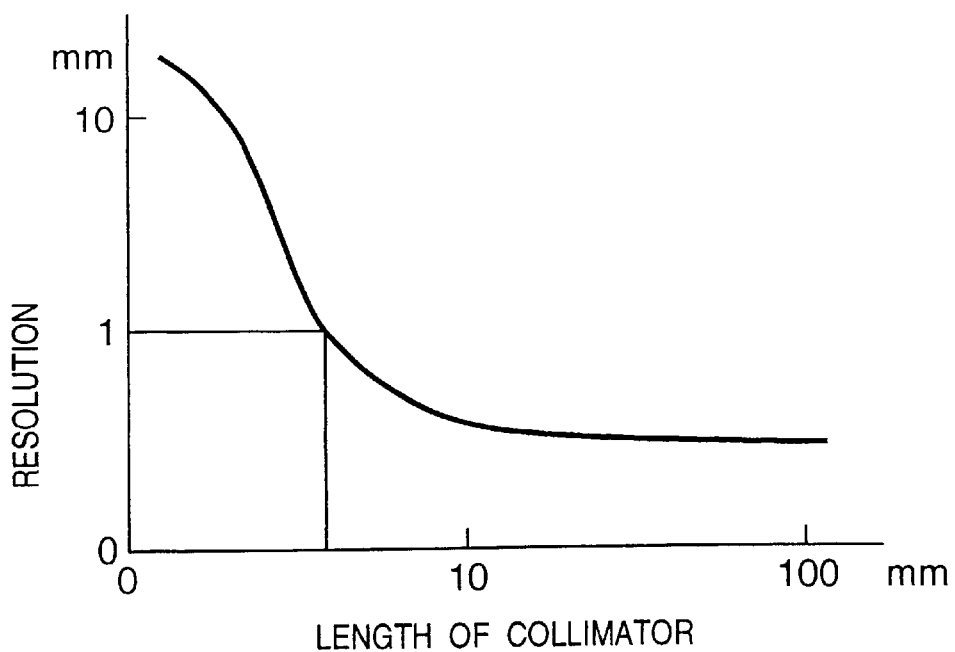
FIG. 10 is a graph showing the relation between the length and resolution of the aforementioned collimator.
Figure 11:
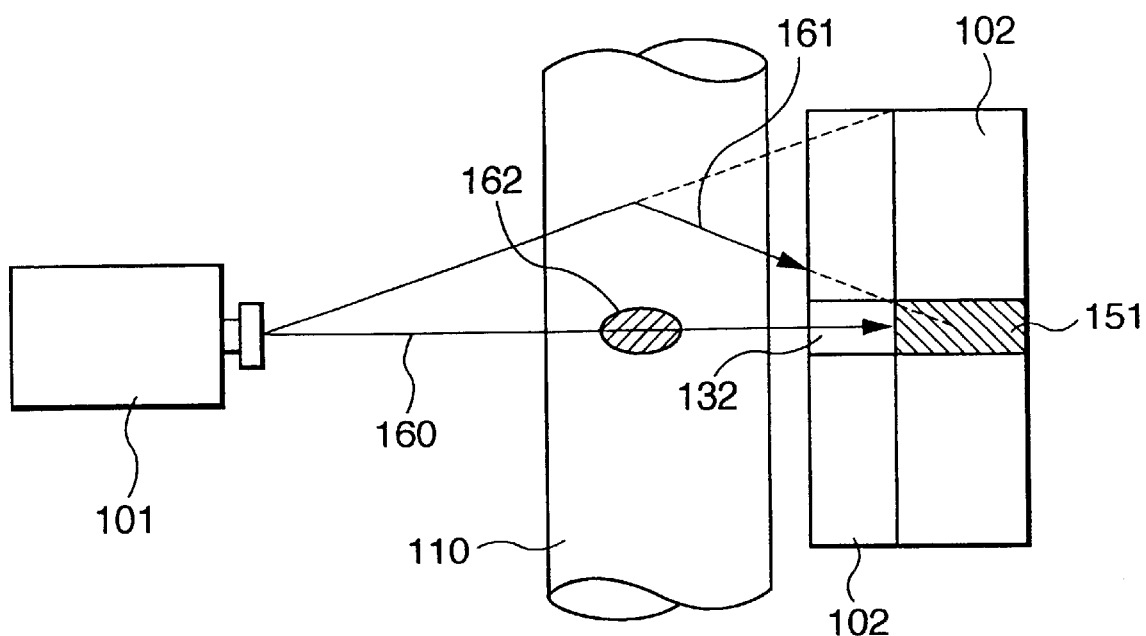
FIG. 11 is a diagram for explaining the behavior of scattered X-rays in the apparatus of the present invention.

The relation between the length of the collimator 102 constituting the present invention and the resolution thereof will be explained by referring to FIGS. 10 and 11. FIG. 10 is a graph showing the relation between the length and resolution of the collimator 102 of the present invention. FIG. 11 is a diagram showing the behavior of scattered X-rays 161 causing a reduction in the resolution in the apparatus of the present invention. The apparatus of the present invention uses high-energy X-rays having high penetrability to inspect a large structure. Therefore, the performance of the collimator 102 arranged in front of the scintillators 151 affects the resolution strongly.

The reason for this will be explained hereunder by referring to FIG. 11.

For simplification of explanation, FIG. 11 shows a case wherein one scintillator 151 is provided and one defect 162 exists on the straight line connecting the scintillator 151 and the accelerator 101 which is a heat source. The scintillator 151 measures the intensity of direct X-rays 160 passing through the defect 162. In this case, to detect the presence or absence of the defect 162, it is necessary to recognize an intensity difference of the direct X-rays 160 between the presence and absence of the defect 162. The resolution can be divided into the following two cases depending on the size of the defect 162.

(1) When the size of the defect 162 is within a range covered by one scintillator 151, the resolution is expressed by the size of the defect 162 which is a limit of recognition of the intensity difference.

(2) When the size of the defect 162 extends over ranges covered by two or more scintillators 151, the resolution is expressed by the size of the defect 162 which is a limit of recognition of the intensity difference by the scintillators 151 covering the defect 162 and the scintillators 151 not covering the defect 162.

As factors disturbing recognition of the intensity difference, there are an electrical factor of the measurement circuit and a factor caused by the scattered X-rays 161, and the resolution can be improved by controlling the sum of these factors. A countermeasure for the electrical factor will be omitted because it is not within the range of the present invention.

A countermeasure for the factor caused by the scattered X-rays 161 will be explained further hereunder. The scattered X-rays 161 are generated, for example, inside the inspection object 110. The scattered X-rays 161 have lower energy than that of the direct X-rays 160, but have high penetrability, and they may pass through the inspection object 110, reach the scintillator 151, and be detected by the scintillator 151. This signal is superimposed on a signal generated by the direct X-rays 160 and disturbs the measure of the intensity of the direct X-rays. To control such a factor caused by the scattered X-rays 161, it is effective to utilize the collimator 102 having a collimator pore 132 in front of the scintillator 151. The collimator 102 has a function of absorbing the scattered X-rays 161 which attempt to pass through a portion other than the collimator pore 132, thereby preventing the scattered X-rays 161 from being detected by the scintillator 151.

As a material of the collimator 102, it is necessary to select a material suited to absorption of the scattered X-rays 161. For example, an alloy including tungsten or a material having a large atomic number and a high density, such as gold or platinum, is most suitable.

It is desirable for the collimator 102 to be longer. However, a problem arises in that, when the collimator 102 is made longer, the weight of the main unit of the collimator 102 increases, the size of apparatus increases, and the cost of the collimator 102 increases. Therefore, it is important to find a most suitable length. To obtain a most suitable value of the length of the collimator 102, the relation of the length to the resolution is important.

FIG. 10 is a graph showing the relation between the length and resolution of the collimators 102. In this case, the resolution means the typical length (a square root of the area of pore) of the collimator pore. As the collimator 102 becomes longer, the resolution improves. However, when the length exceeds a certain value, further improvement in the resolution will not appear. Although, when no collimator is provided, the resolution becomes lower, such an arrangement may be put to practical use depending on the application. When a resolution of about 1 mm is desired, FIG. 10 shows that the length of the collimator 102 should be 5 mm at a minimum.

A signal generated by the scattered x-rays 161 passing through the collimator 102 is outputted from each scintillator 151. However, the undesirable influence of these scattered X-rays 161 can be eliminated by suitable correction.

Figure 12:
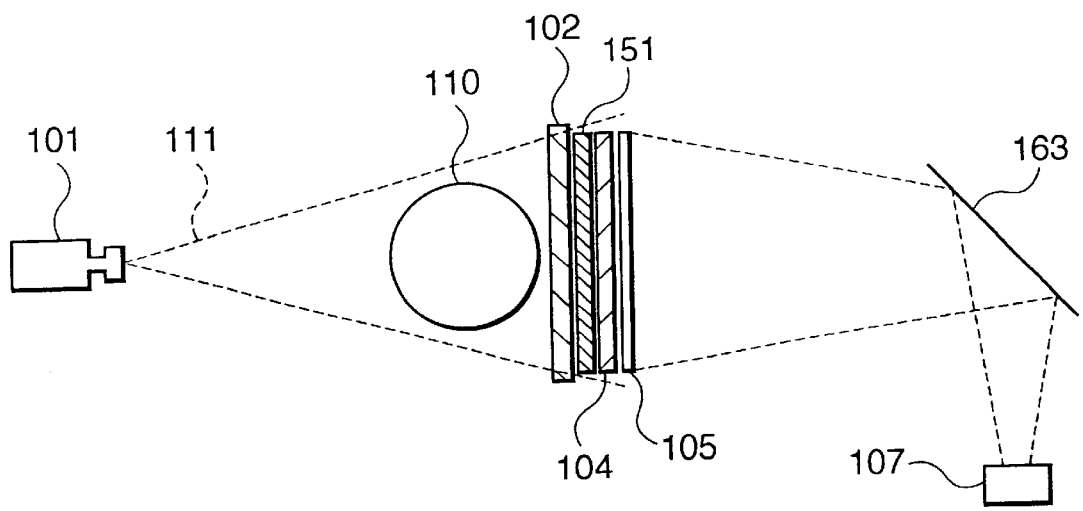
FIG. 12 is a diagram showing an example of the constitution of a high-energy X-ray inspection apparatus to which the present invention is applied.

FIG. 12 shows an example of the constitution of a high-energy X-ray inspection apparatus to which the present invention is applied. In this example, X-rays generated by the accelerator 101 are irradiated onto the inspection object 110, such as a pier, and a part thereof is transmitted or scattered. Among the transmitted X-rays, scattered X-rays are shielded by the collimator 102 and only the X-rays going straight on enter the scintillator. The scintillator has a long structure coinciding with the advancing direction of the X-rays specified by the collimator and is structured so as to absorb high-energy X-rays efficiently and to emit light.

Photons generated by light emission from the scintillator arranged two-dimensionally are converted to electrons on the photo electric surface and are then amplified by the micro-channel plate (MCP) 104 installed immediately behind it. Electrons outputted from the MCP are converted to photons on the fluorescent screen and light is transmitted in space. The light is received by the imaging camera (CCD) 107 via a mirror 163. This example has advantages in that the sensitivity is high because light emitted by the scintillator 151 is amplified by the MCP 104 installed immediately behind it and the apparatus can be configured by a simple structure because the optical path from the fluorescent screen 105 to the CCD camera 107 includes only the mirror 163.

Figure 13:
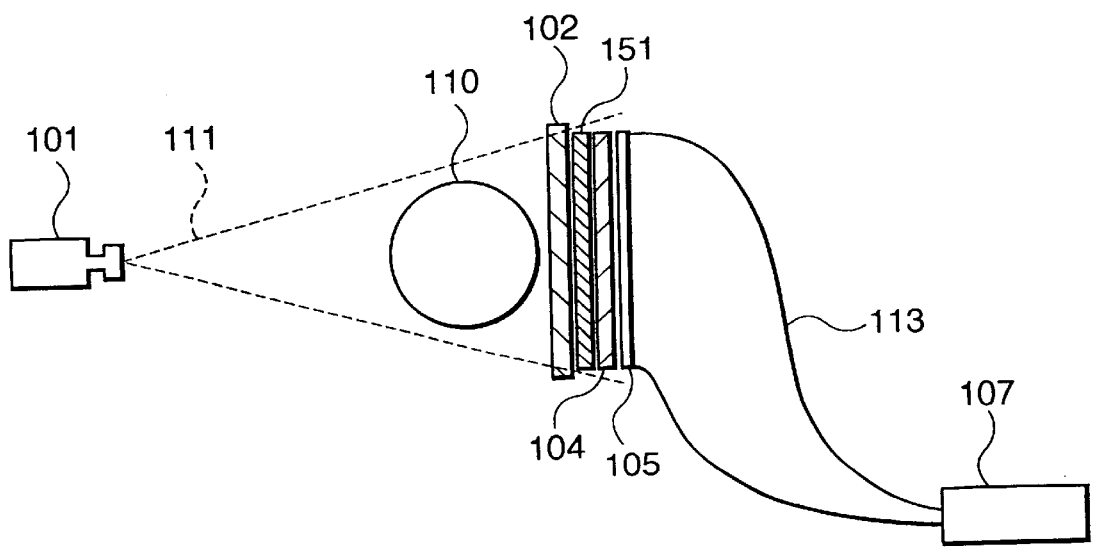
FIG. 13 is a diagram showing another example of the constitution of a high-energy X-ray inspection apparatus to which the present invention is applied.

FIG. 13 shows an example in which the optical path from the fluorescent screen 105 to the CCD camera 107 comprises an optical fiber bundle 113 in the example shown in FIG. 12. Among the X-rays 111 generated in the accelerator 101, which is a high-energy X-ray generator, X-rays scattered by the inspection object 110, such as a pier, are shielded by the collimator 102 and only X-rays going straight on are detected by the scintillator 151 arranged two-dimensionally. Light emitted by each scintillator 151 is converted to electrons on the photo electric surface and then amplified by the micro-channel plate (MCP) 104. The electrons 157 outputted from the MCP 104 are converted to photons on the fluorescent screen 105 and the image is reduced by the optical fiber bundle 13 and transmitted to the CCD camera 107.

This example has an advantage in that the sensitivity is high because light emitted by the scintillator 151 is amplified by the MCP 104 installed immediately behind it. Since the optical path from the fluorescent screen 105 to the CCD camera 107 comprises the optical fiber bundle 113, positional accuracy in the optical path is not required and imaging with high precision can be realized. Furthermore, a high-energy X-ray inspection apparatus which withstands vibration and can be moved and installed easily can be provided.

A constitution wherein the aforementioned scattering is shielded by the collimator 102, and the X-rays 111 going straight on are led directly to the image intensifier, and direct radiography is performed can be achieved easily. FIG. 2 shows the constitution and concurrent use of the collimator 102 of the present invention to effectively realize a high-performance inspection apparatus.

Figure 14:
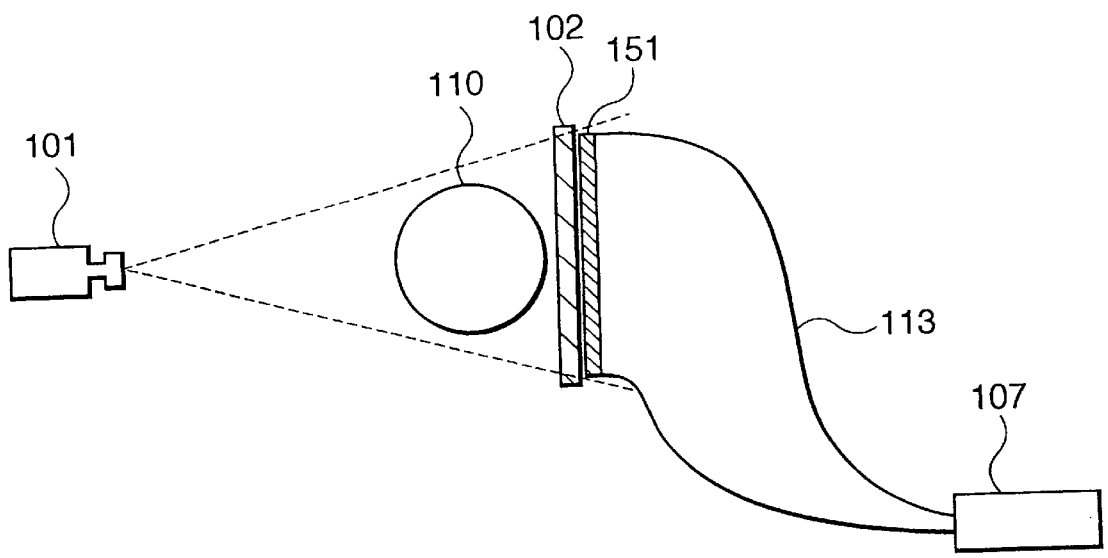
FIG. 14 is a diagram showing still another example of the constitution of a high-energy X-ray inspection apparatus to which the present invention is applied.
Figure 15:
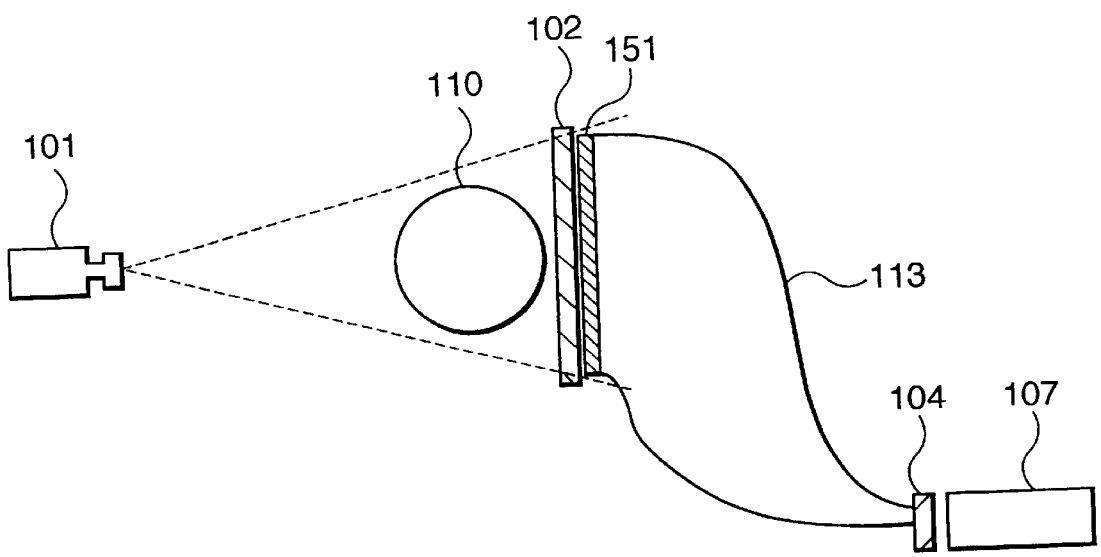
FIG. 15 is a diagram showing an example of the constitution of a high-energy X-ray inspection apparatus to which the present invention is applied.

FIGS. 14 and 15 show examples of the constitution of a high-energy X-ray inspection apparatus to which the present invention is applied. These are embodiments in which a sufficient light intensity is obtained. In the example shown in FIG. 14, photons generated by light emission by the scintillator 151 arranged two-dimensionally are transmitted by the optical fiber bundle 113 and received by the CCD camera 107. In the embodiment shown in FIG. 15, the MCP 104 is arranged in front of the CCD camera 107 and the sensitivity is improved. Some CCD cameras contain the MCP 104 and such a case is included in this embodiment.

The arrangements shown in FIGS. 14 and 15 are examples wherein a sufficient light intensity is obtained and the object of the present invention can be accomplished by a simple structure. In a large size X-ray inspection apparatus of the present invention having these features, one detection system is provided for each pixel of an image and imaging with high precision is made possible.

Figure 16:
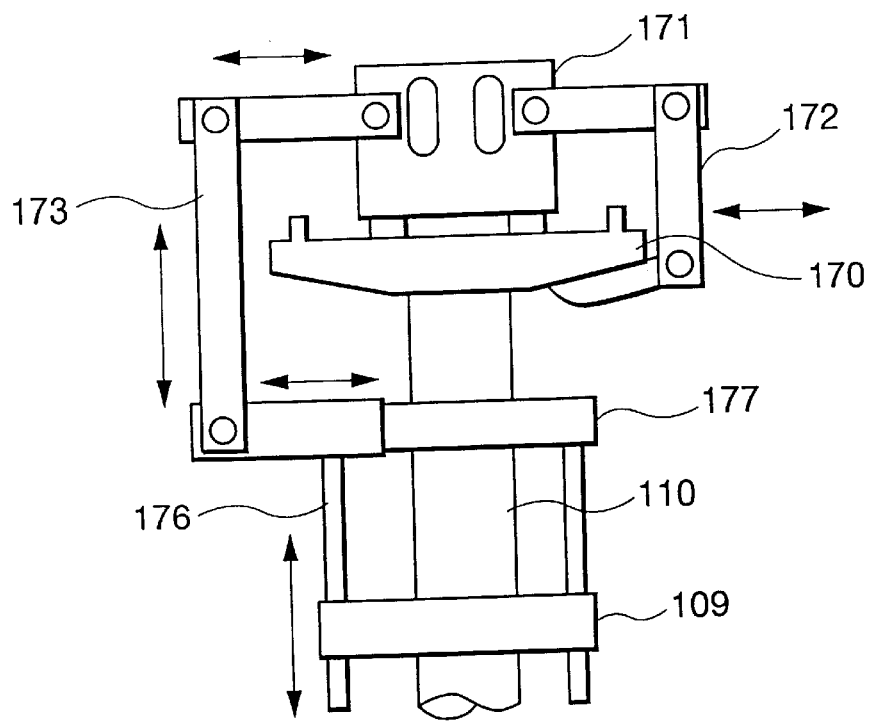
FIG. 16 is a diagram showing an example of the X-ray inspection apparatus of the present invention being applied to the inspection of a pier.

An embodiment wherein an X-ray inspection apparatus of the present invention is applied to inspection of a pier is shown in FIG. 16. When inspection of a pier is desired, an X-ray inspection apparatus transfer facility for installing an X-ray inspection apparatus at the pier is required.

In this embodiment, a method of installing an X-ray inspection apparatus at a pier, which is the inspection object 110, from a road 170 will be described.

The X-ray inspection apparatus transfer facility comprises a transfer operation room 171, a hook 172, a forklift 173, a vertical drive facility 176, a vertical drive facility positioning stage 177, and a stage 109. The X-ray inspection unit is supported on the stage 109. A method of moving the X-ray inspection apparat us to the inspection position from the road will be explained by referring to this drawing.

An inspection operator installs the hook 172 from the transfer operation room 171 on the road at the pier as shown in the drawing. This hook 172 is a facility for counter-balancing the equipment to prevent the room 171 with the transfer device from tipping over. After the hook 172 is installed, the inspection operator moves the vertical drive facility positioning stage 177 from the transfer operation room 171 to the top of the inspection position of the pier, which is the inspection object 110, using the forklift 173. At this time, the vertical drive facility is folded and the stage 109 is fixed to the bottom of the vertical drive facility positioning stage 177.

When the vertical drive facility positioning stage 177 moves to the specified position, the vertical drive facility positioning stage 177 is fixed to the pier, which is the inspection object 110, with a fixing jig. This fixing plays a role for assisting the positioning by the forklift. After the vertical drive facility positioning stage 177 is fixed to the pier, which is the inspection object 110, the stage on which the X-ray inspection apparatus is placed is lowered and stopped at the inspection position by the vertical drive facility 176. After stopping, the X-ray inspection is executed and the stage is moved to the next inspection position in the same way.

Figure 17:
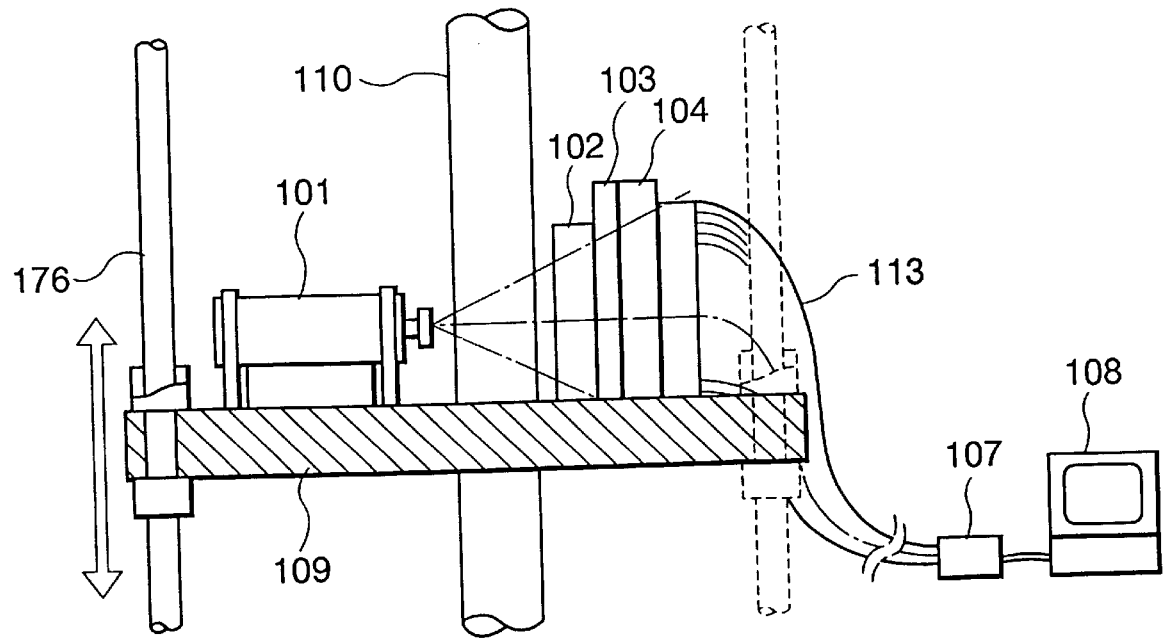
FIG. 17 is a diagram showing details of the stage of the X-ray inspection apparatus of the present invention.

The stage 109, which is moved by the vertical drive facility 176, is shown in FIG. 17 in detail. The X-ray detector system comprising the accelerator 101, which is an X-ray source, the collimator 102, the scintillation detector 103, and the MCP 104 are installed on the stage 109. The X-ray source 101 and the X-ray detector system are positioned and fixed to the stage 109 beforehand so that the X-ray detection system is directed toward the X-ray source with the pier being interposed therebetween.

When the stage 109 is stopped at the inspection position, the apparatus starts X-ray inspection. The X-ray inspection is carried out by radiating a conical beam of X-rays generated from the accelerator 101 toward the inspection object 110 and by detecting X-rays attenuating and passing inside the inspection object 110 using the X-ray detection system. The detected signal enters the CCD camera 107 via the optical transfer fibers 106 and is converted to a digital signal and outputted by the arithmetic display unit as an image. By this inspection method, the inspection object 110 enters a state such that X-ray radiography is performed and a defect, such as a crack inside the inspection object 110, can be discovered from the image.

Figure 18:
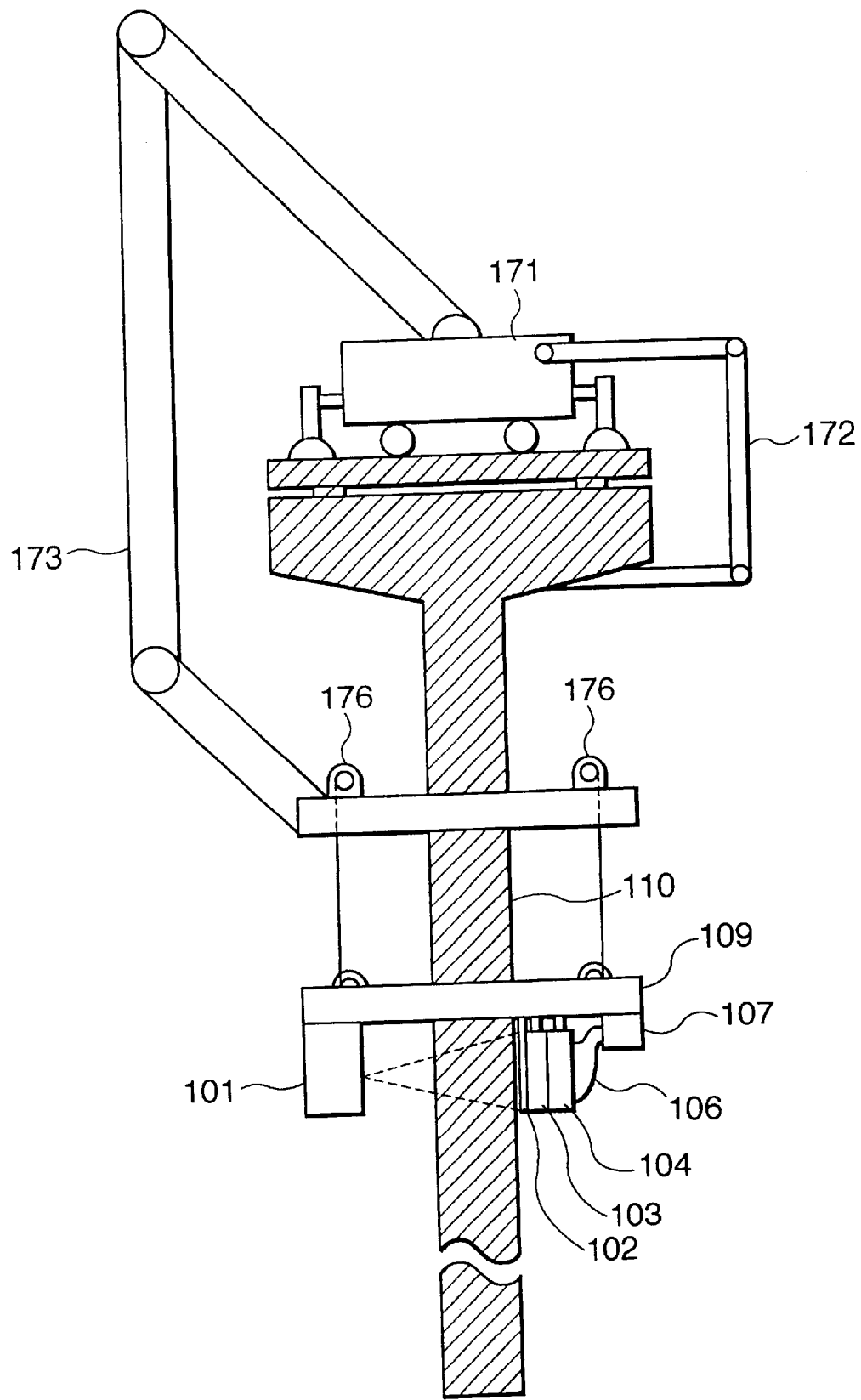
FIG. 18 is a plan view showing another example that the X-ray inspection apparatus of the present invention is applied to inspection of a pier.

FIG. 18 shows another example wherein the X-ray inspection apparatus of the present invention is applied to inspection of a pier. This embodiment is an example of the embodiment shown in FIG. 16. The basic constitution is the same as that shown in FIG. 16 except that the vertical drive facility 176 uses a wire cable. The X-ray detection system of the accelerator 101 and the collimator 102 is fixed to the bottom of the stage 109. By doing this, the lowering extent of the stage 109 (U shaped) can be made greater and even a pier with a height of several tens of meters can be inspected throughout.

Figure 19:
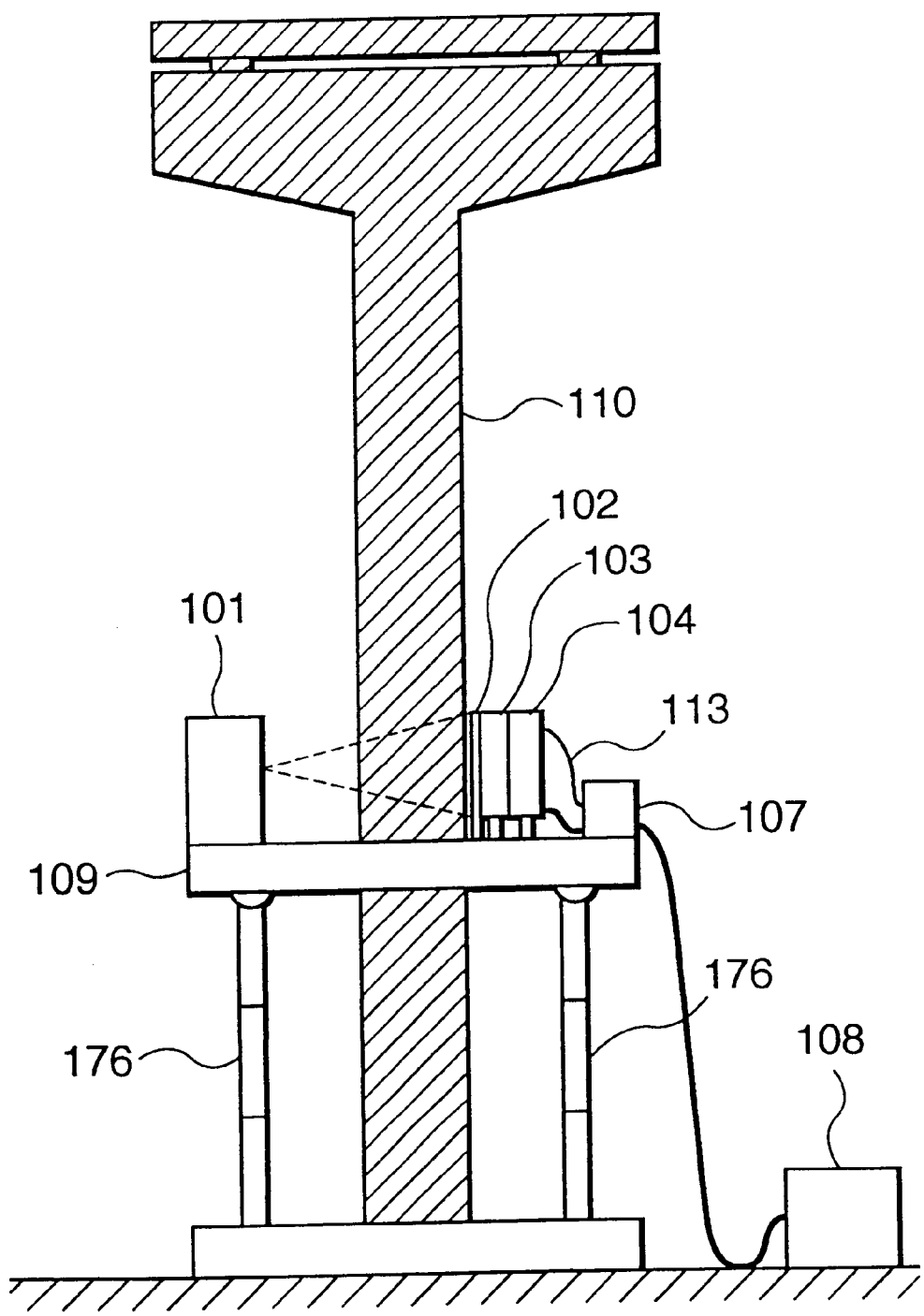
FIG. 19 is a plan view showing still another example that the X-ray inspection apparatus of the present invention is applied to inspection of a pier.

FIG. 19 shows a further embodiment wherein the X-ray inspection apparatus of the present invention is applied to inspection of a pier. This embodiment shows a case in which the inspection apparatus is installed from the ground unlike the case wherein the inspection apparatus is installed from a road above the inspection object 110. The X-ray inspection apparatus of the present invention using these X-ray inspection apparatus transfer facilities can realize fluoroscopic inspection of a large structure and an inspection system thereof easily, which cannot be realized conventionally.

Figure 20A:
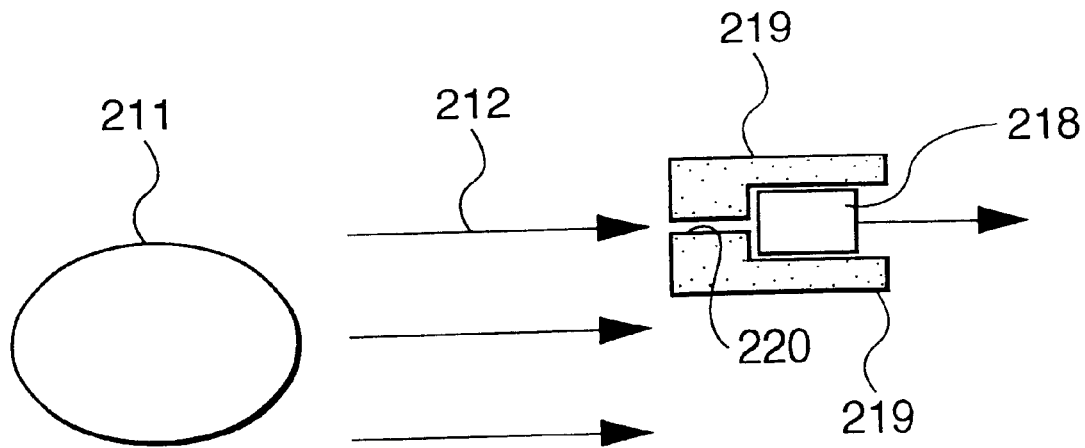
FIGS. 20a and 20b are diagrams showing an arrangement for measuring a two-dimensional radiation distribution using scanning by the detector.
Figure 20B:
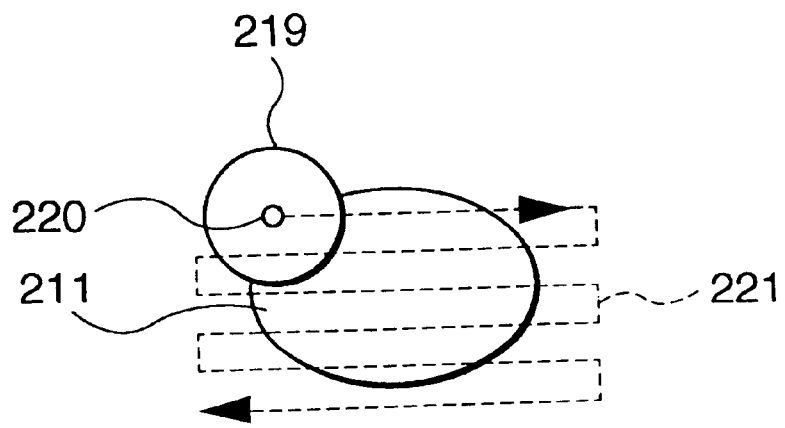

A conventional two-dimensional radiation detection device is generally a radiation distribution measurement device for moving a radiation detector having a collimator within the measurement range and measuring the distribution of radiation from an object. A two-dimensional radiation distribution measurement device of this type is shown in FIGS. 20a and 20b.

A radiation detector 218 is installed behind a through hole 220 of a collimator 219 and detects radiation from a measurement object 211. In this case, radiations to be detected are limited to radiations passing through the collimator. Namely, only radiations of a component in the direction of the through hole of the collimator are detected, so that the detected radiation intensity reflects the radiation intensity on the surface of the measurement object. Therefore, the radiation detector moves, as shown by a dashed line in FIG. 20b, and measures the radiation distribution on the surface of the measurement object However, this system has a disadvantage in that measurement takes a lot of time.

An apparatus for measuring a two-dimensional radiation distribution is disclosed in JP-A-3-48188 and JP-A-6-201835 In the apparatus described in the former publication, plastic scintillation fibers are arranged in multi-layer sheets and the radiation incident position is specified by taking concurrent calculation with other layers. In the apparatus described in the latter publication, a radiation detector comprising mostly a scintillator is inserted into through holes arranged in a matrix state in the collimator and a two-dimensional radiation distribution is obtained.

Since the former uses plastic scintillation fibers, the sensitivity for high-energy X-rays is particularly low. The positional resolution is limited by the diameter of plastic scintillation fibers. The latter has a defect in that the positional resolution is limited by the interval of the through holes.

When the diameter of plastic scintillation fibers or the interval of the through holes is reduced to improve the positional resolution, which is limited by the diameter of plastic scintillation fibers or the interval of the through holes in a collimator like this, defects are caused in that the sensible volume of the scintillator is reduced and the sensitivity lowers or high-energy X-rays cannot be detected.

Therefore, in accordance with the present invention, to make it possible to measure a more-detailed radiation distribution in a short time without causing a reduction in sensitivity, a radiation detector with a collimator which is arranged two-dimensionally moves along a set surface.

The radiation detector with a collimator which is arranged two-dimensionally moves along a surface where the radiation detector is arranged by a driver attached to the detector and measures the radiation distribution. The operation is set so as to interpolate the arrangement of the detector. The detector moves as set and then measures the radiation intensity. Results of several radiation intensity measurements are overlapped and a radiation intensity distribution is created.

Figure 21:
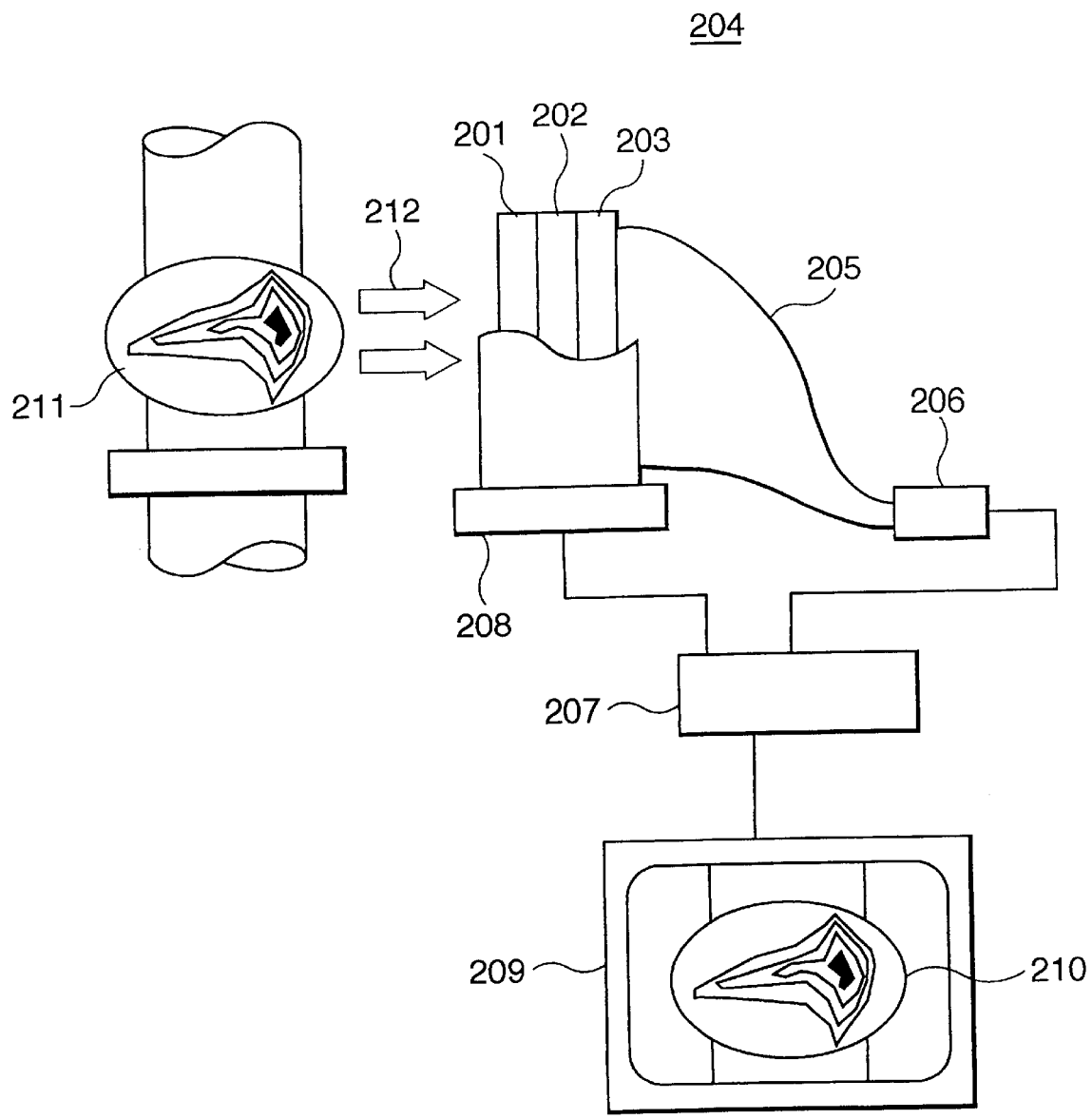
FIG. 21 is a diagram illustrating radiation distribution measurement.

An embodiment illustrating these features will be explained hereunder by referring to the drawings. FIG. 21 shows an example of the two-dimensional radiation detector of this embodiment. In this example, a case in which plastic scintillation fibers are used as a radiation detection unit will be explained. However, a scintillator type radiation detector or a semiconductor type radiation detector also can be used as a radiation detection unit.

Figure 22:
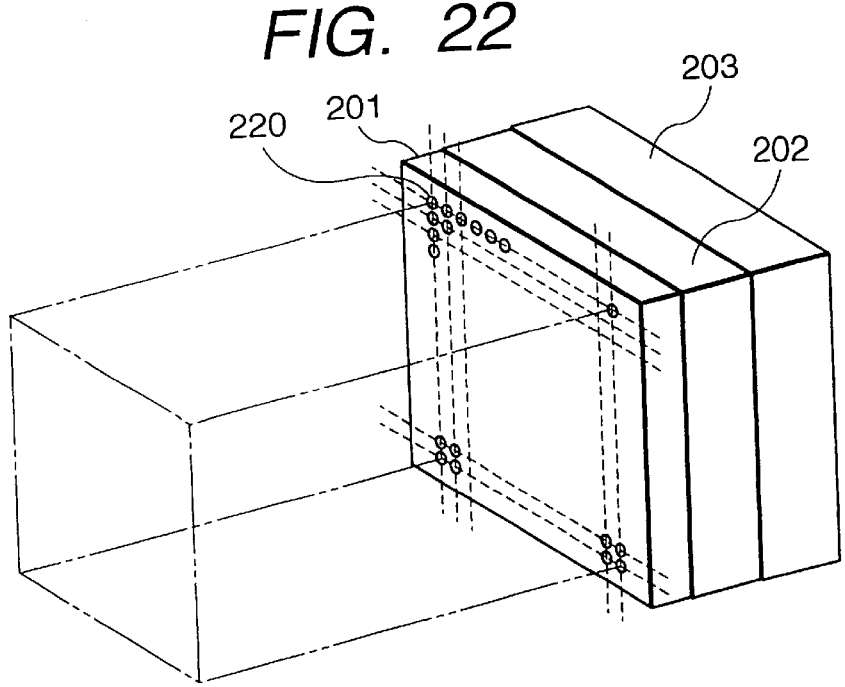
FIG. 22 is a diagram illustrating the collimator unit and radiation detection unit of the aforementioned embodiment.
Figure 23:
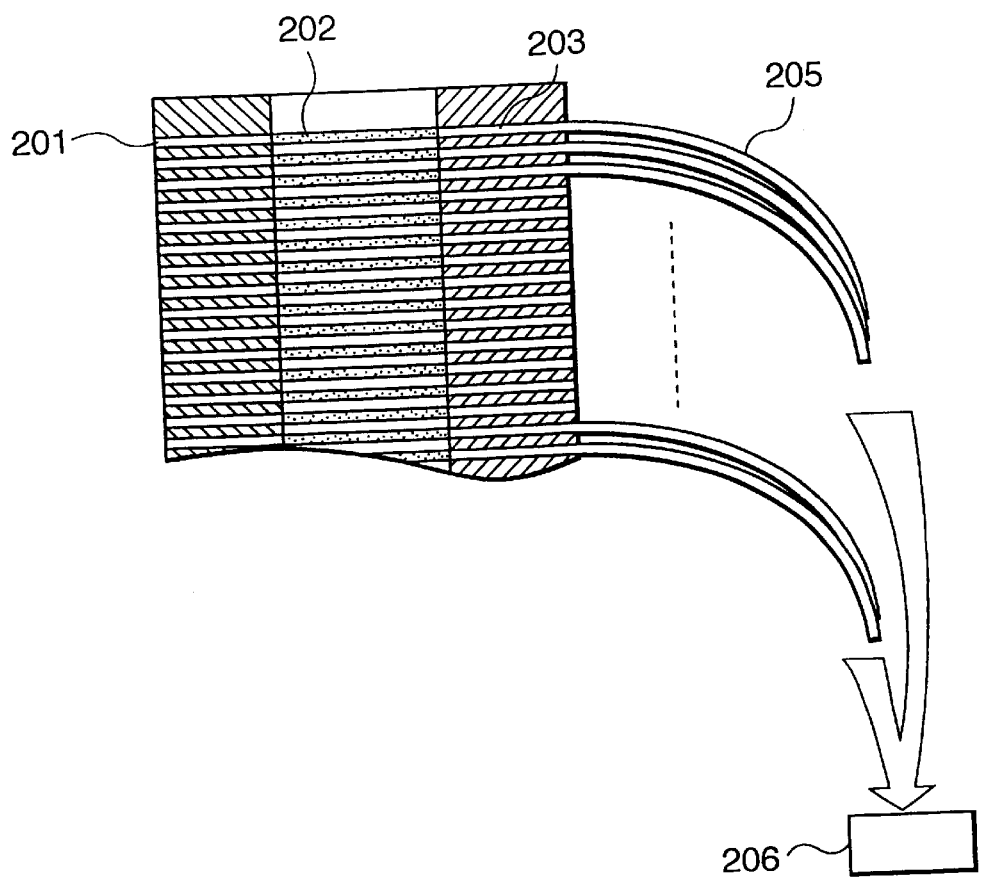
FIG. 23 is a cross sectional view of the aforementioned collimator unit and radiation detection unit.

The outline of the radiation detection unit 204 of FIG. 21 is shown in FIG. 22, and the cross sectional view thereof is shown in FIG. 23. The radiation detection unit 204 comprises a collimator 201, plastic scintillation fibers 202, and a connection unit 203. Behind the through holes of the collimator 201, the plastic scintillation fibers 202 are positioned and installed, respectively.

The connection unit 203 is installed at one end of the plastic scintillation fibers 202 and connected to transmission optical fibers 205. The transmission optical fibers 205 are connected to a photoelectric conversion element 206. The plastic scintillation fibers 202, the connection unit 203, the transmission optical fibers 204, and the photoelectric conversion element 206 are shielded from light so as to prevent the entrance of external light. The detected light outputted from each of the transmission optical fibers 205 is measured by the photoelectric conversion element 206. The measured results are inputted to an arithmetic unit 207. The arithmetic results are displayed by a display unit 209. A displayed image 210 displays the intensity distribution of the radiation using color tones.

The direction of the radiation 212 from a measurement object 211 is selected by the collimator 201, so that a clear radiation distribution on the surface of the measurement object 211 can be obtained. In a radiation distribution measurement of a detection object radiating high-energy X-rays, the influence of radiation scattered by a peripheral structure cannot be ignored, so that it is indispensable to improvement of the positional resolution to install a collimator and eliminate the influence of scattered X-rays.

Figure 24:
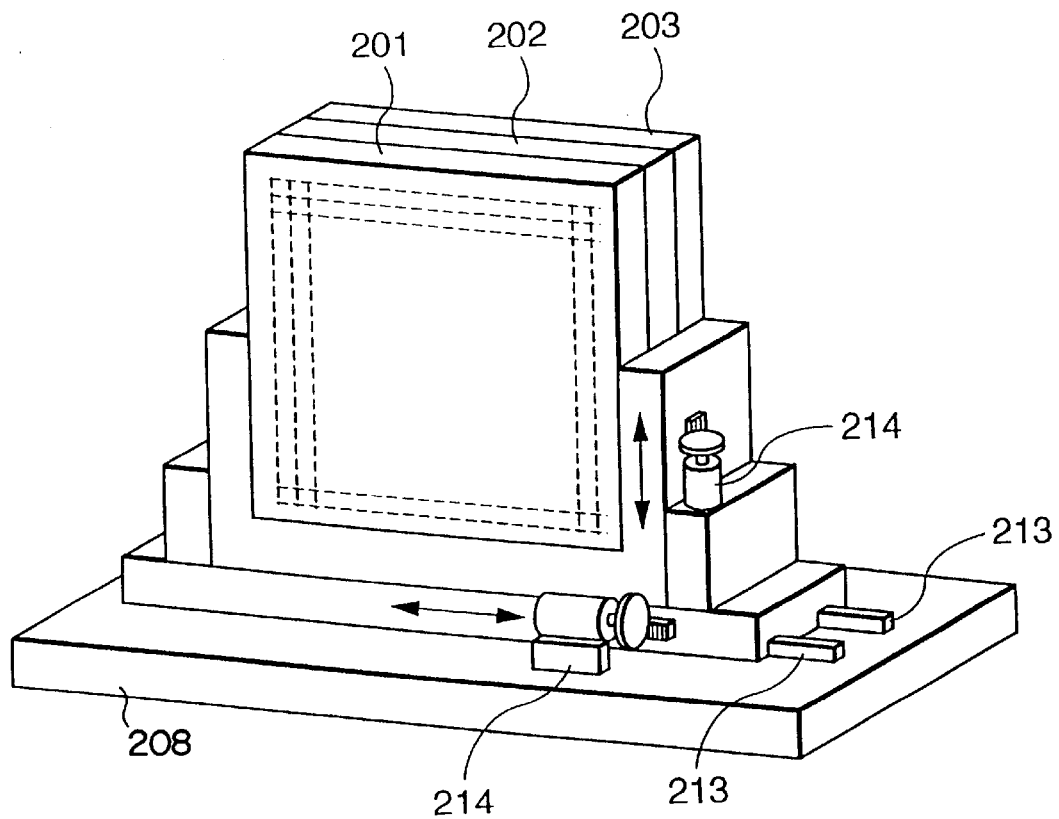
FIG. 24 is a perspective view of a driver for controlling the positions of the aforementioned collimator unit and radiation detection unit.
Figure 25:
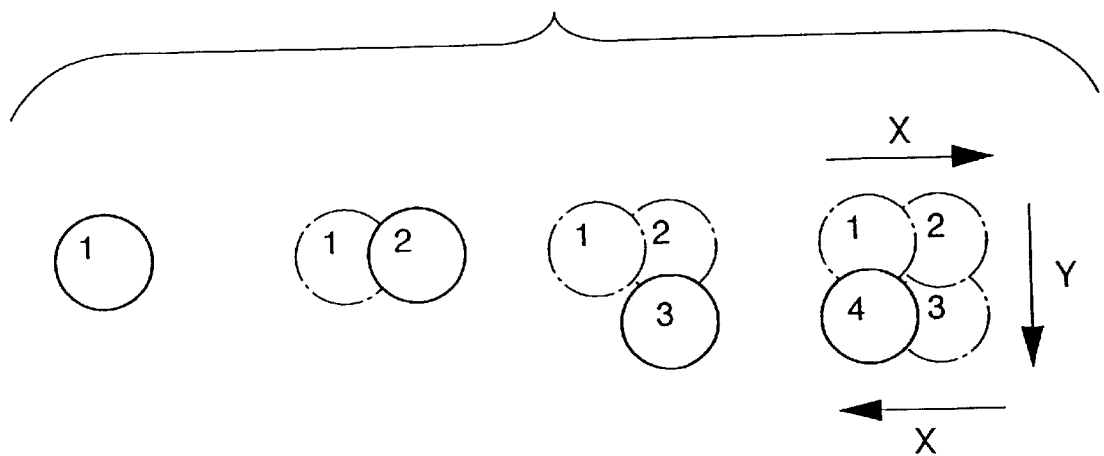
FIG. 25 is a diagram illustrating the resolution of the detection unit when the aforementioned collimator unit and radiation detection unit move finely.

The arithmetic unit 207 is connected to a driver 208 which carries the radiation detection unit 204. The general details of the driver 208 are shown in FIG. 24. The driver supports the overall radiation detection unit, so that the detection unit can be moved finely near the surface where the detectors are arranged. Guide rails 213 and motors 214 are attached to a base of the driver and the moving direction is determined by the rotation of the motors 214. After the measurement at a first position ends, the driver 208 receives a signal from the arithmetic unit 207 and moves the radiation detecting unit 204 along the surface where the radiation detectors are arranged. An example of the operation is shown in FIG. 25.

In this example of the operation, the radiation detector position of one of the plural detectors is set at each vertex of a square with the measurement positions being in contact with each other. A circle in the drawing indicates one radiation detector position in the detection unit. After a measurement is made at a first measurement position, the driver 208 moves the detection unit in the X direction. The movement distance is ½ of the inter-detector distance (the position 2 in the drawing). When this movement ends, the driver 208 makes a second measurement. Thereafter, the driver 208 moves the detection unit in the Y direction. The movement distance is ½ of the inter-detector distance (the position 3 in the drawing). When this movement ends, the driver 208 makes a third measurement. Thereafter, the driver 208 moves the detection unit in the—(minus) direction. The movement distance is ½ of the inter-detector distance (the position 4 in the drawing). When this movement ends, the driver 208 makes a fourth measurement.

Figure 26:
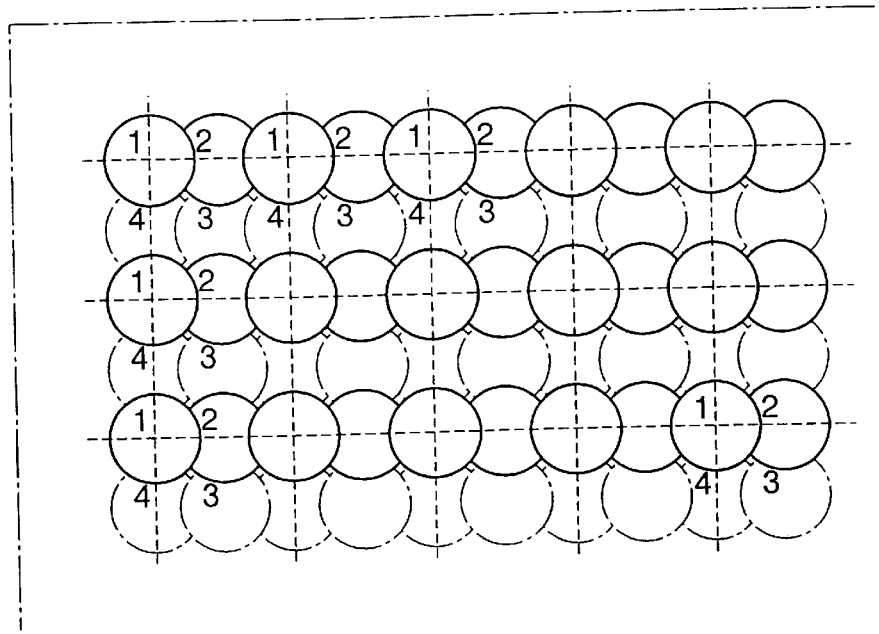
FIG. 26 is a diagram illustrating the resolution as a whole after the operation shown in FIG. 25 is repeated.

The four measurement positions, which are established in an overlapping manner by the plural radiation detectors, are shown in FIG. 26. The movement distance and the number of measurements can be changed according to the arrangement of the radiation detectors and the desired target position resolution. All of the detectors move while the respective relative positions thereof are maintained, so that a detector position can be specified easily. When a plurality of measured results are overlapped, the radiation intensity can be measured more minutely using a simple driver and a more clear two-dimensional radiation distribution can be created.

Figure 27:
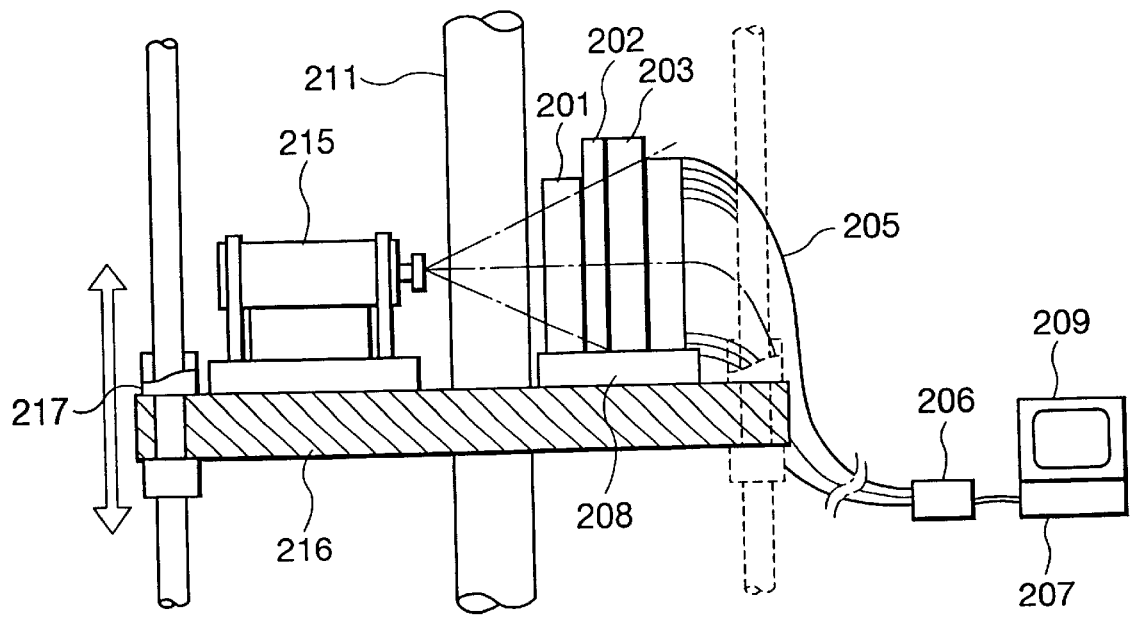
FIG. 27 is a diagram of an example when the present invention is applied to a bridge inspection apparatus.

FIG. 27 shows an example of this embodiment being applied to a radiographic testing (RT) apparatus for pier inspection. An RT apparatus for pier inspection is disclosed in Japanese Patent Application Laid-Open 8-82330, which was applied for by the applicant of this application. As an embodiment of the present invention, the radiation detector portion of this RT apparatus for pier inspection comprises a two-dimensional radiation detector.

X-rays radiated from an accelerator type X-ray generator 215 are irradiated onto a radiographic object 211 and transmitted X-rays thereof are measured by the two-dimensional radiation detector of the present invention. The radiation detector of this embodiment is installed so that it is positioned on a spherical surface having a vertex at the X-ray generation position and the radiation detection unit moves so as to interpolate the measurement position on the spherical surface where the radiation detectors are arranged. The whole apparatus is carried on a support 216 which is moved up and down by a vertical movement facility 217. X-rays are not generated during movement of the support 216 and the radiation detection unit, but they are generated in synchronization with measurement of radiation, so that a leakage dose at the periphery can be reduced.

According to this embodiment, in the two-dimensional radiation distribution measurement device with a collimator, the distribution is measured by moving a radiation detector along the surface where the radiation detectors are arranged by the driver attached to the detector, so that an apparatus for measuring a detailed two-dimensional radiation distribution in a short time can be obtained.

A large-size non-destructive inspection apparatus as mentioned previously is disclosed in JP-A-5-302997. The patent application discloses that this apparatus can be applied to inspection of a 200-1 oil drum filled with metal scraps or concrete and has a tomographic and radiographic function. In the apparatus described in JP-A-6-269439, it is pointed out that positioning of the X-ray generator is important and a means for such positioning in a short time is described. With respect to alignment accuracy, the size of the X-ray focus is very small, such as 1 mm in diameter or less, and positioning within an allowance of about +0.1 mm is necessary. The number of parameters to be positioned is 6 including the X position, Y position, and Z position of the orthogonal coordinates and the angles round the axes. If the alignment is insufficient, the output of the detector lowers and images become unclear.

For example, if an object is significantly dislocated, the output of the detector becomes zero and only noise produced by the circuit is measured. In a case of only longitudinal dislocation, an image is obtained in which the center thereof can be seen clearly, but the periphery thereof becomes blurred gradually. As mentioned above, there is a relation between displacement and an image, and so it is possible to detect a displacement from an obtained image and correct the dislocation. However, while an object is being imaged, the resulting image may become non-uniform due to reflection from an internal structure of the inspection object, so that the influence of the inspection object and the influence of displacement cannot be entirely separated from each other.

As mentioned above, to obtain a normal image, alignment is very important. It is also difficult to effectively use the imaging result of an inspection object for this purpose.

With respect to a pier inspection apparatus, the following performances are required. (1) X-rays must transit concrete with a thickness of 1 m, (2) the inspection must be completed in a short time so as to reduce the leakage of X-rays into the peripheral environment, and (3) a reduction in quality of an image due to scattered X-rays from an inspection object should be prevented.

Figure 28:
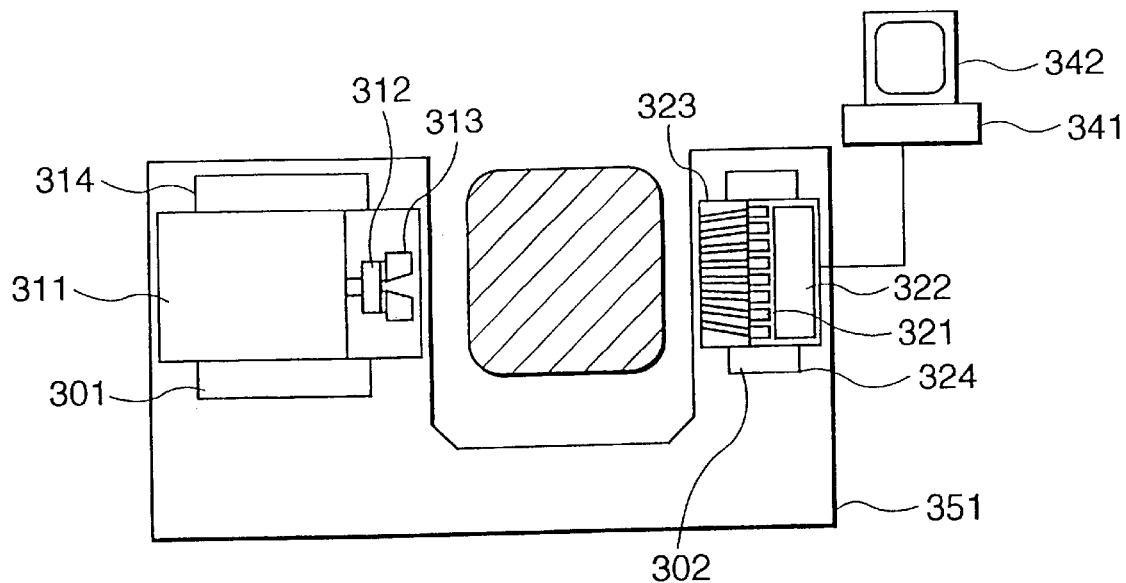
FIG. 28 is a diagram showing still another embodiment of the present invention.

To realize these requirements, the following structural features are provided, as shown in FIG. 28: (1) a high-energy X-ray generator using an electron beam accelerator so as to generate X-rays having a strong penetrability, (2) a collimator attached to the X-ray generator so as to reduce the leakage of X-rays into the peripheral environment, (3) a highly sensitive solid detector (semiconductor detector, scintillation detector, etc.) and a signal processor capable of completing the inspection in a short time, (4) a collimator attached to the X-ray detection device which is able to reduce the amount of X-rays scattered by an inspection object for entering the detector, and (5) an image display unit and a processing unit comprising computers mostly to evaluate inspection results in a short time.

However, in the prior art, it is a precondition that the x-ray generator and the x-ray detection device are carried on a common frame where they are installed and fixed (hereinafter called a first prior art). In the state where the inspection object is removed, that is, even if the X-ray generator and the detection device are separated from each other, because the X-ray generator can be seen directly from the X-ray detection device, alignment is possible (hereinafter referred to a second prior art).

In FIG. 28, for purposes explanation, some parts are shown in section. They are generally installed inside the frame and cannot be seen.

An X-ray generator 301 and an X-ray detection device 302 are arranged on opposite sides of a pier. Namely, in the same way as the principle of X-ray radiography, assuming that the pier is like the chest of a human, an X-ray film is used in the X-ray detection device 302, the human (pier) stands facing the X-ray detection device 302, and X-rays are irradiated by the X-ray generator 301 from the back thereof.

Therefore, in an image obtained by the X-ray detection device 302, as seen from the X-ray inspection, a shadow of reinforcing bars inside the pier and inner structures equivalent to bones and organs of a human are seen.

Unlike a human, to transmit and image a structure comprising high-density materials, such as reinforcing bars and concrete in a pier, X-rays having very high energy and high brightness are necessary. Such X-rays can be generated by using an electron beam accelerator 311 (when a high-energy electron beam accelerated by the electron beam accelerator 311 collides with a target 312, high-energy X-rays are generated by breaking radiation).

However, such X-rays affect the human body greatly, so that they are generally used in a radiation controlled area shielded from X-rays. Therefore, to decrease leakage of X-rays to the outside as much as possible, it is necessary to prevent unnecessary X-ray leakage and reduce the exposure dose of X-rays as much as possible. For that purpose, to prevent unnecessary X-ray leakage, a collimator 313 for restricting the irradiation range of X-rays is attached to the X-ray generator 301.

To complete the inspection with a small exposure dose, the sensitivity of the X-ray detection device 302 is increased and the detection efficiency is improved. For that purpose, a solid detector 321 having a sensitivity 1000 times or more than that of an X-ray film is used. For the solid detector 321, a semiconductor detector (silicon semiconductor detector, germanium semiconductor detector, GaAs compound semiconductor detector, CdTe compound semiconductor detector, etc.) or a scintillation detector can be used.

For the scintillation detector, a combination of photodiodes for receiving a material (NaI (Tl) crystal, $CdWO_4$ crystal, $ZnWO_4$ crystal, $Bi_4Ge_3O_{12}$ crystal, etc. or a plastic scintillator with a fluorescent material added) emitting light by incidence of radiation and its fluorescence and converting it to an electric signal is used.

A signal from the solid detector 321 is amplified by a signal processor 322 and the signal intensity thereof is converted to digital data and sent to a computer 341. The computer 341 creates a fluoroscopy image of the pier from the measured data and displays it on a display unit 342.

The electron beam accelerator 311 generates X-rays like a pulse, so that it is necessary to operate the X-ray generator 301 and the X-ray detection device 302 in synchronization with each other. By one irradiation of X-rays, measured data equivalent to the number of solid detectors 321 can be obtained. A fluoroscopic image of the pier comprises, for example, 1000 meshes. If, for example, 1000×1000 solid detectors 321 are densely arranged one-dimensionally, image data of one line is obtained by one irradiation of X-rays and when 1000 irradiations and measurements are carried out by moving sequentially the solid detectors 321 at regular intervals perpendicular to the arrangement direction, one fluoroscopic image is completed. If, for example, 1000× 1000 solid detectors 321 are densely arranged two-dimensionally, one fluoroscopic image is completed by one irradiation of X-rays.

When the solid detectors 321 detect only X-rays substantially along a straight line connecting the focus of the X-ray source and the center of each solid detector, a fluoroscopic image indicates the internal structure of the pier accurately. However, when X-rays scattered inside the pier enter the solid detectors 321, the contribution of scattered X-rays gets mixed in the true detector output as noise and the resulting image becomes blurred. Therefore, to prevent scattered X-rays from entering the solid detectors 321 as much as possible, a post collimator 323 having a slit for passing only a necessary part of the X-rays is installed on the input side of the solid detectors 321. By installation of the post collimator 323, scattered X-rays are prevented from reaching the detectors and a clear image can be obtained.

The post collimator 323 is mounted so that each slit coincides with a respective solid detector 321 as much as possible and is generally fixed or positioned with respect to the X-ray detection device 302. It is necessary that the intersecting point of the center lines of the slits coincides with the focus of X-rays of the X-ray generator 301 as much as possible. Unless the two coincide with each other, the output of the solid detectors 321 lowers and a clear image cannot be obtained. As a result, positioning of the X-ray generator 301 and the X-ray detection device 302, that is, proper alignment, becomes very important. Therefore, when it is intended to move and use the X-ray generator 301 and the X-ray detection device 302, they are fixed to a common frame 351. In this case, if the frame 351 is bent or twisted, the alignment is lost, so that a frame sufficient strength is necessary. Namely, the apparatus becomes considerably larger than the mere total size of the X-ray generator 301 and the X-ray detection device 302.

As mentioned above, in the first prior art wherein the X-ray generator and X-ray detection device are mounted on a common frame, a problem arises that when they are taken and used out of doors, to reserve the strength of the frame, the whole apparatus becomes larger in scale. In the second prior art wherein the X-ray generator and X-ray detection device are separated from each other, a problem arises in that, in the state when the two cannot be seen from each other, such as during inspection of a large pier, no alignment can be realized.

Therefore, according to this embodiment, the X-ray generator and X-ray detection device are separated from each other to increase the mobility out of doors, and so the whole apparatus is made smaller, which enables non-destructive inspection of a large structure, such as a pier, and the two devices can be installed on opposite sides of an inspection object and be aligned with high precision.

For this purpose, according to this embodiment, the non-destructive inspection apparatus, comprising an X-ray generator and an X-ray detection device arranged in opposite side of an inspection object, has a relative position measuring means for measuring the positional relation between the X-ray generator and the X-ray detection device, an X-ray generator attitude control means for adjusting the X-ray generator to a position determined from the mutual geometric structure for generation and detection of X-rays of the X-ray generator and X-ray detection device, and an X-ray detection device attitude control means.

For the aforementioned relative position measuring means, the non-destructive inspection apparatus has a reference position control device independent of the X-ray generator and X-ray detection device. For relative position measurement, the reference position control device has three or more fixed measuring points, and the X-ray generator has three or more fixed measuring points, and the X-ray detection device has three or more fixed measuring points.

For distance measurement between measuring points, the non-destructive inspection apparatus has an arrival time measuring means using an ultrasonic pulse and a means for measuring the air temperature at the measurement location.

For distance measurement, the non-destructive inspection apparatus has a means for generating a predetermined pattern signal and a means for discriminating and detecting the pattern signal. Furthermore, for distance measurement, the non-destructive inspection apparatus has a generation means for generating a pattern signal several times and a means for adding and averaging a received signal in synchronization with the generation timing.

When the aforementioned relative position measuring means is provided, the X-ray generator and X-ray detection device can be separated from each other. By doing this, there is no need to install them on a common frame and the apparatus can be made smaller. Since they can be separated from each other, the apparatus can be also applied to a case in which the inspection area is large like a large pier and it is necessary to move the inspection location. Furthermore, there is no need to manufacture an apparatus for each type of structure, and so the same apparatus can be used to inspect many structures.

When a third position reference device is provided as a relative position measuring means, in a location where the generator and the detection device are not visible from each other, that is, in the state wherein a structure is positioned between the two, the relative position can be measured. Radiography can be performed independently on the size and shape of the structure. Furthermore, in an inspection which is carried out by moving the imaging location little by little, as is required for inspection of a large structure, radiography can be performed immediately without taking time for alignment for each movement.

When three or more fixed measuring points are provided in the position reference device, three or more fixed measuring points in the X-ray generator, and three or more fixed measuring points in the X-ray detection device for relative position measurement, the positions of the X-ray generator and X-ray inspection apparatus can be obtained by a principle similar to that of triangular surveying.

When an arrival time measuring means using an ultrasonic pulse and a measuring means for the air temperature at the measurement location are provided for distance measurement between measuring points, the accuracy of the distance measurement can be improved further.

When a means for generating a predetermined pattern signal and a means for discriminating and detecting a pattern signal are provided for distance measurement, the accuracy of distance measurement can be improved further.

Furthermore, when a generation means for generating a pattern signal several times and a means for adding and averaging a received signal in synchronization with the generation timing are provided, the accuracy of distance measurement can be improved further.

This embodiment will be explained hereunder by referring to the drawings.

Figure 29:
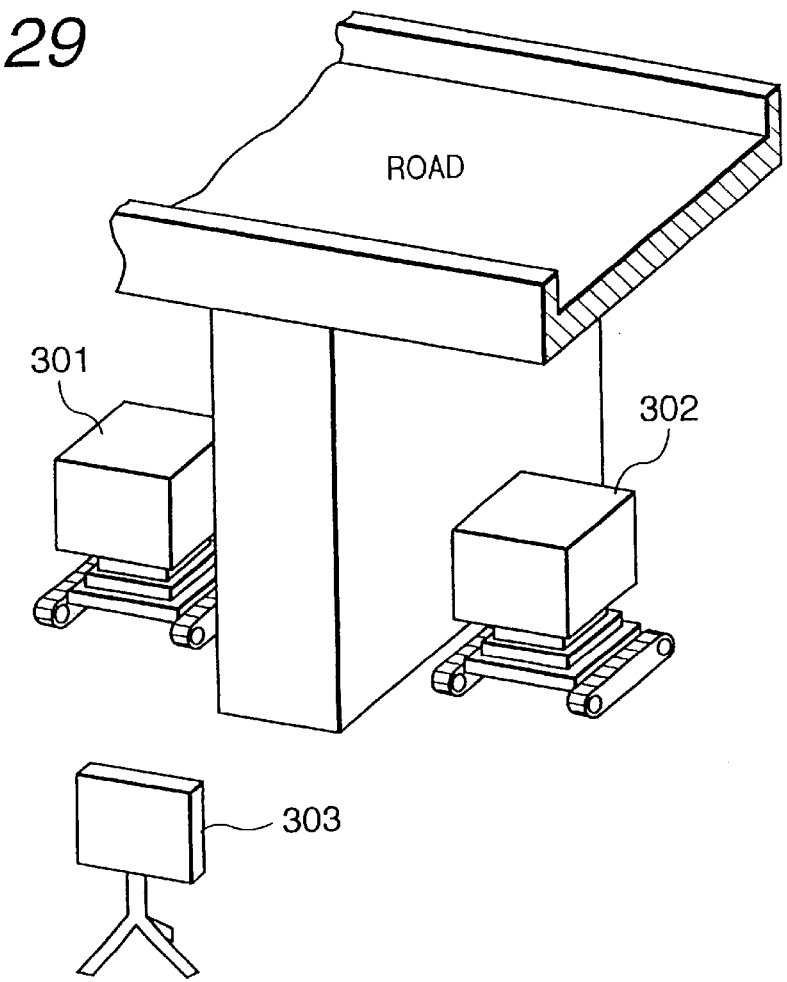
FIG. 29 is a diagram showing an arrangement for inspection of a pier.

FIG. 29 is a schematic view of the embodiment of the present invention. This example shows the status of inspection of a pier of a high-level road.

The X-ray generator 301 and the X-ray detection device 302 are installed on the ground on both sides of the pier. For alignment of the two, a level gauge 303 is installed beside the pier. The relative position of the X-ray generator 301 and the X-ray detection device 302 is determined via the level gauge 303. The X-ray generator 301 and the X-ray detection device 302 can move independently and during inspection of a large pier, the measuring position can be changed by the respective self moving means.

When the measuring position is moved, the relative position is measured each time and adjusted by the attitude control means (not shown in the drawing) attached to each device so as to execute alignment. When the alignment process ends, the inspection at the position is executed and when the inspection ends, the apparatus moves to the next location. The X-ray generator 301 and the X-ray detection device 302 are operated remotely from a control car which is not shown in the drawing. Or, they can be operated independently of each other by the operation means of the devices.

Figure 30A:
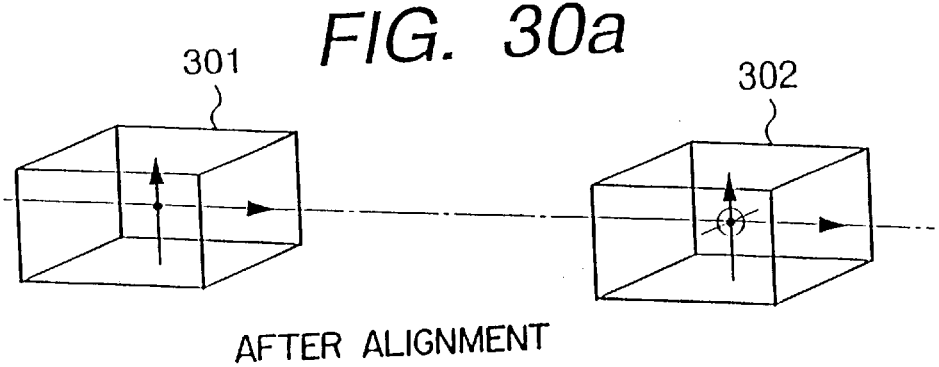
FIGS. 30a and 30b are diagrams for explaining alignment.
Figure 30B:
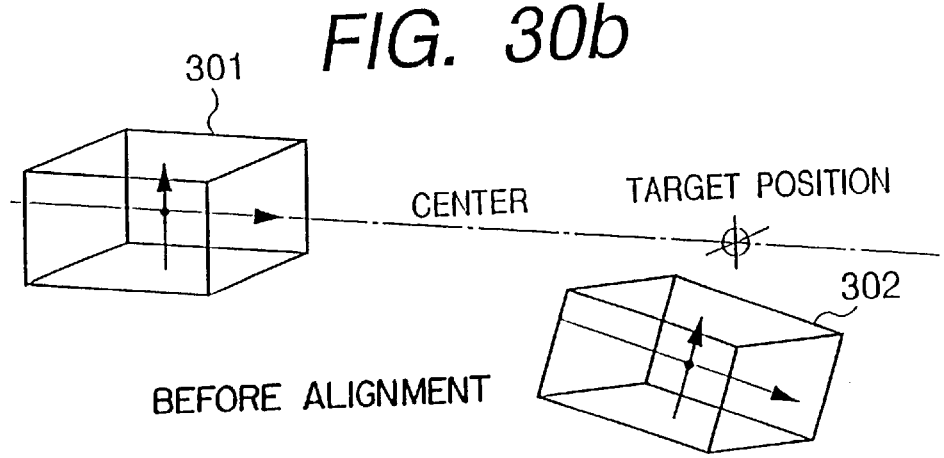

FIGS. 30a and 30b are illustrations for effecting alignment. The frames in the drawing indicate the X-ray generator 301 and the X-ray detection device 302 and the arrows in the drawing indicate the axis of X-ray generation direction and a perpendicular axis of each device. The intersection point of the arrows of the X-ray generator 301 indicates the focus of X-rays and the intersection point of the arrows of the X-ray detection device 302 indicates the center point of the detector. FIG. 30a is a drawing of the relative arrangement after alignment representing a perfect alignment status. FIG. 30b is a drawing of the relative arrangement before alignment representing an imperfect alignment status. The target position on the center line and the origin of the X-ray detection device are generally not only deviated from each other like this, but they are also twisted. Therefore, there are six parameters requiring correction at a maximum including displacements in the directions of the three orthogonal axes and twists around the axes. Therefore, the attitude controller is required to have a means for correcting these six parameters at a maximum.

Figure 31:
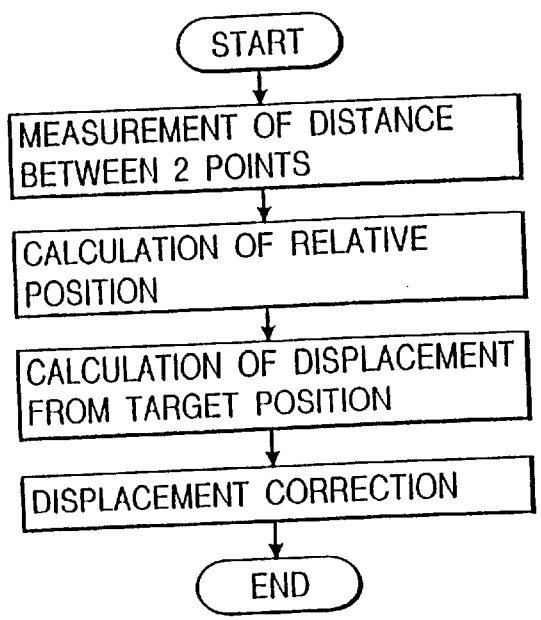
FIG. 31 is a flow chart showing an embodiment of the displacement correction procedure.

FIG. 31 is a flow chart showing an embodiment of the displacement correction procedure. A means for measuring the relative position and correcting displacement will be explained briefly.

To measure the relative position, the distance is measured between the measuring points fixed in a level gauge, X-ray generator, and X-ray detection device. Firstly, to obtain the positional relationship between the level gauge and the X-ray generator, 3-point distances are required, respectively, that is, 9 combinations of data in total are required. Furthermore, to obtain the positional relationship between the level gauge and the X-ray detection device, 3-point distances are required, respectively, that is, 9 combinations of data in total are required also in this case. Therefore, 18 combinations of distances are measured.

Next, the relative position is calculated from the respective 9 combinations of data by a principle similar to that of triangular surveying. In this case, it is necessary to obtain the relative positions of 3 points of each device beforehand, that is, the relative positions of 3 points fixed in the level gauge, the relative positions of 3 points fixed in the X-ray generator, and the relative positions of 3 points fixed in the X-ray detection device.

A displacement from the target position is calculated from relative position calculation results. In this case, 6 parameters at a maximum are obtained. The position is corrected according to this displacement value by using the attitude control means. To execute a displacement correction surely, although not shown in the flow chart, measurement for confirmation and displacement calculation between the calculated relative position and the target position are executed once again. If necessary, measurement is executed even during radiography so as to confirm the presence or absence of a displacement.

Figure 32:
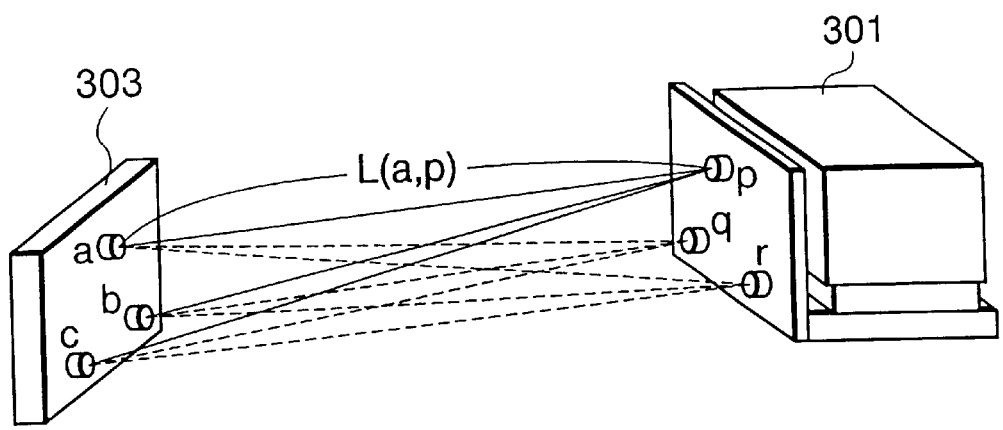
FIG. 32 is a diagram showing the principle of position measurement.

FIG. 32 is an illustration showing the principle of position measurement. The relative position is determined three-dimensionally by a principle similar to that of triangular surveying.

In the drawing, for explanation, only the relation between the X-ray generator 301 and the level gauge 303 is shown. However, the same may be said for the X-ray detection device, so that the explanation thereof will be omitted. The measuring points in the level gauge 303 are indicated by a, b, and c. Although the positional relationship of the points measuring is optional, it is necessary to set relative positions beforehand. There are measuring methods (not shown in the drawing) available, such as a method using a three-dimensional precision measurement device and a method of deciding the position on the design stage. In the same way, the measuring points in the X-ray generator are indicated by p, q, and r. To determine the relative position, the distances between the three points of the respective devices, that is, 9 combinations of distances including, for example, the distance L (a, p) between the points a and p are measured.

Figure 33:
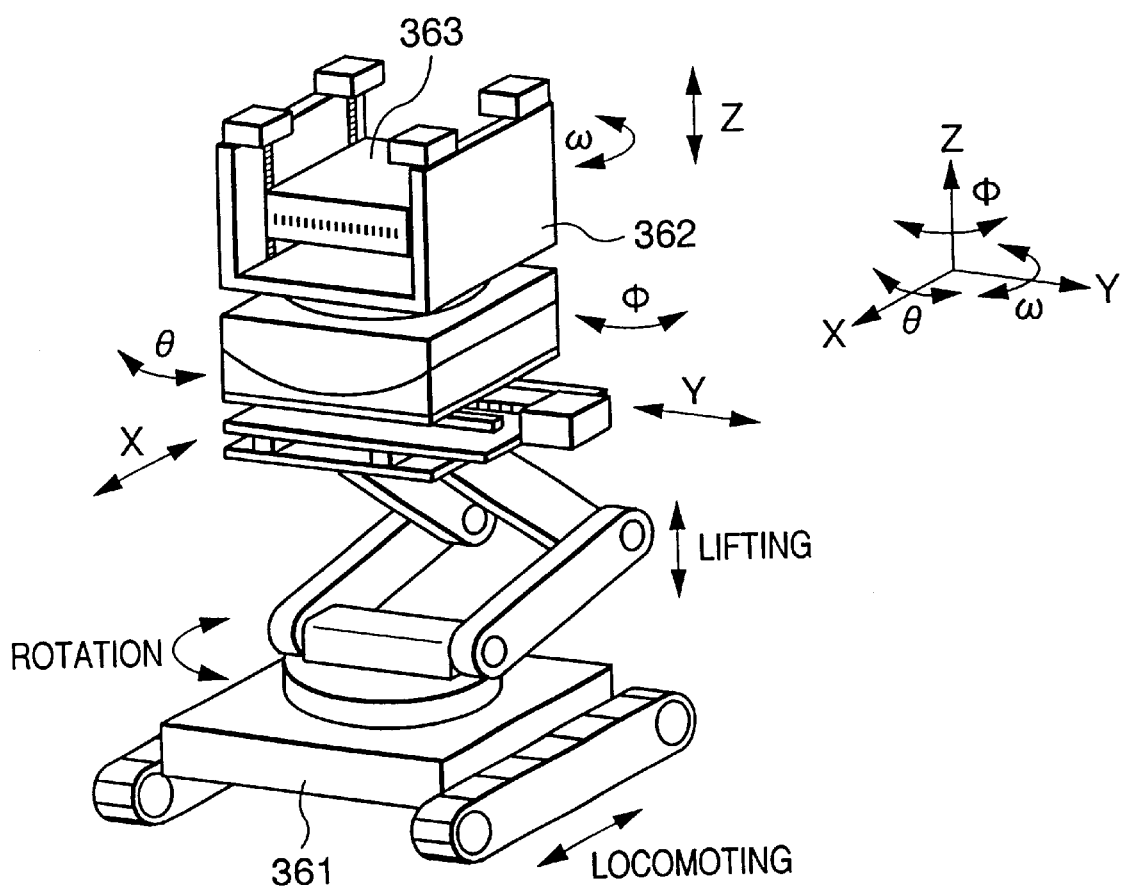
FIG. 33 is a perspective view showing a part of the embodiment of FIG. 32.

FIG. 33 is a perspective view showing this embodiment. Although various combinations of attitude control means are known, only one example is shown. With respect to the control axis type of attitude controller, all the six axes of the X-ray generator 301 and the X-rays detection device 302 are not always necessary, but may be selected and provided as required.

FIG. 33 shows an example of the attitude controller of the X-ray detection device. A detection unit 363 of the X-ray detection device is fixed to an attitude controller 362 and the attitude controller 362 is attached to an arm comprising a rotary device and a lifting device from a ground moving means 361. In the attitude controller 362, a twist through an angle omega around the Z and Y axes can be carried out by a combination of the longitudinal axes advancing concurrently. When the detection unit 363 comprises one-dimensional solid detectors, it is necessary to scan in a direction perpendicular to the arrangement of the solid detectors so as to obtain a fluoroscopic image. This scanning can be executed by a dedicated scanning means not shown in the drawing, but a part of the attitude control means also can be used.

Figure 34:
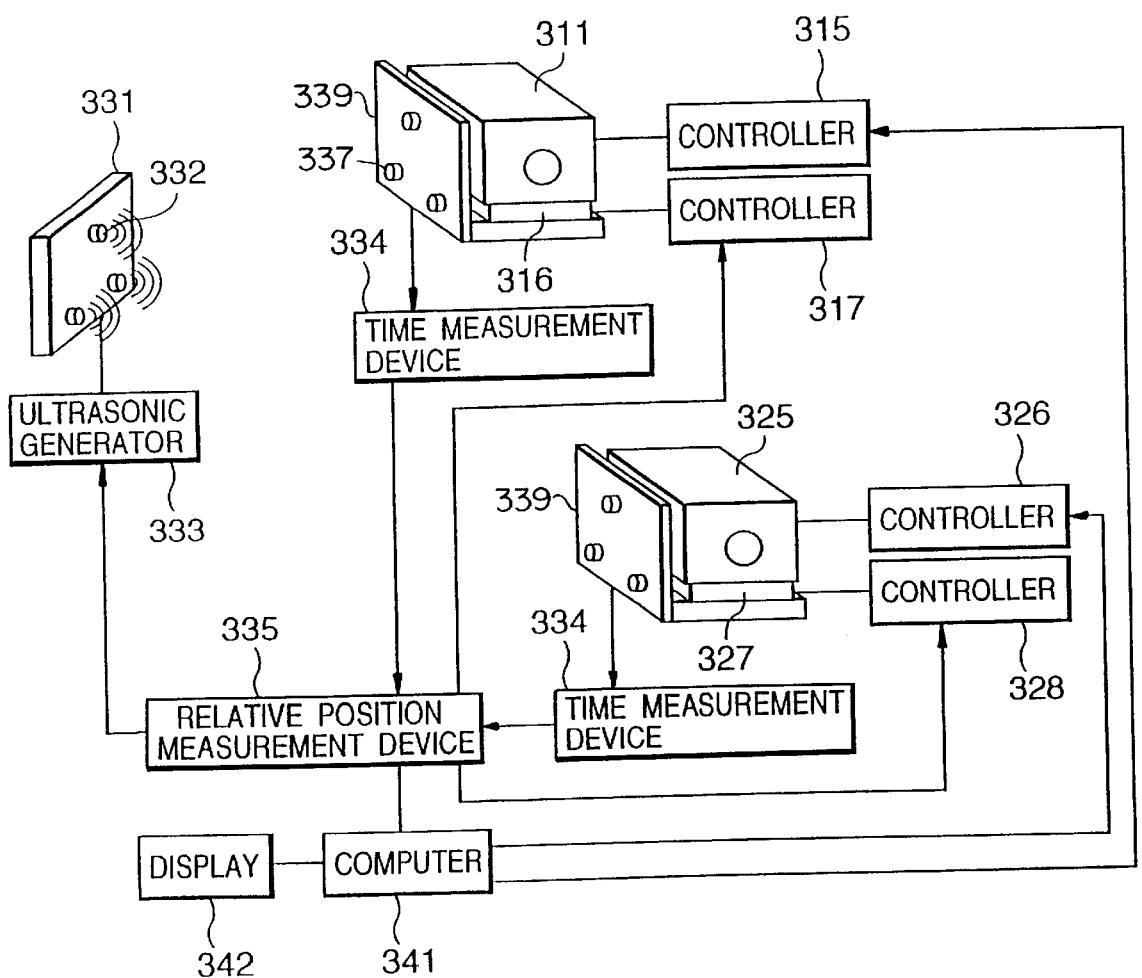
FIG. 34 is a block diagram showing this embodiment.

FIG. 34 is a block diagram showing this embodiment. A distance measuring method based on a calculation using the propagation time of the ultrasonic wave will be indicated below.

An ultrasonic oscillator 332 is fixed to, for example, a level gauge 331 and a respective receiver unit 339 is fixed to the side of each of the X-ray generator 311 and X-ray detection device 325. The distance measurement by ultrasonic waves is based on a calculation using the propagation time and the speed of sound. Generation of ultrasonic waves and measurement of the propagation time are controlled, for example, by a relative position measurement device 335. In response to a trigger signal, ultrasonic waves are generated from the measuring points on the level gauge by an ultrasonic generator 333. Each receiver unit 339 receives ultrasonic waves and a time measurement device 334 measures the propagation time. Measured results are read by the relative position measurement device 335.

The relative position is obtained from 18 combinations of measured data in total and a displacement is calculated. The displacement calculation is carried out by a computer 341 or the relative position measurement device 335. Correction data is sent to controllers 317 and 328 of the attitude control means 316 and 327 according to the displacement so as to execute alignment. When the alignment is completed, the apparatus starts radiography. The measurement is executed, for example, by sending a start signal to a controller 315 of X-ray generator 311 and a controller 326 of X-ray detection device 325.

Figure 35:
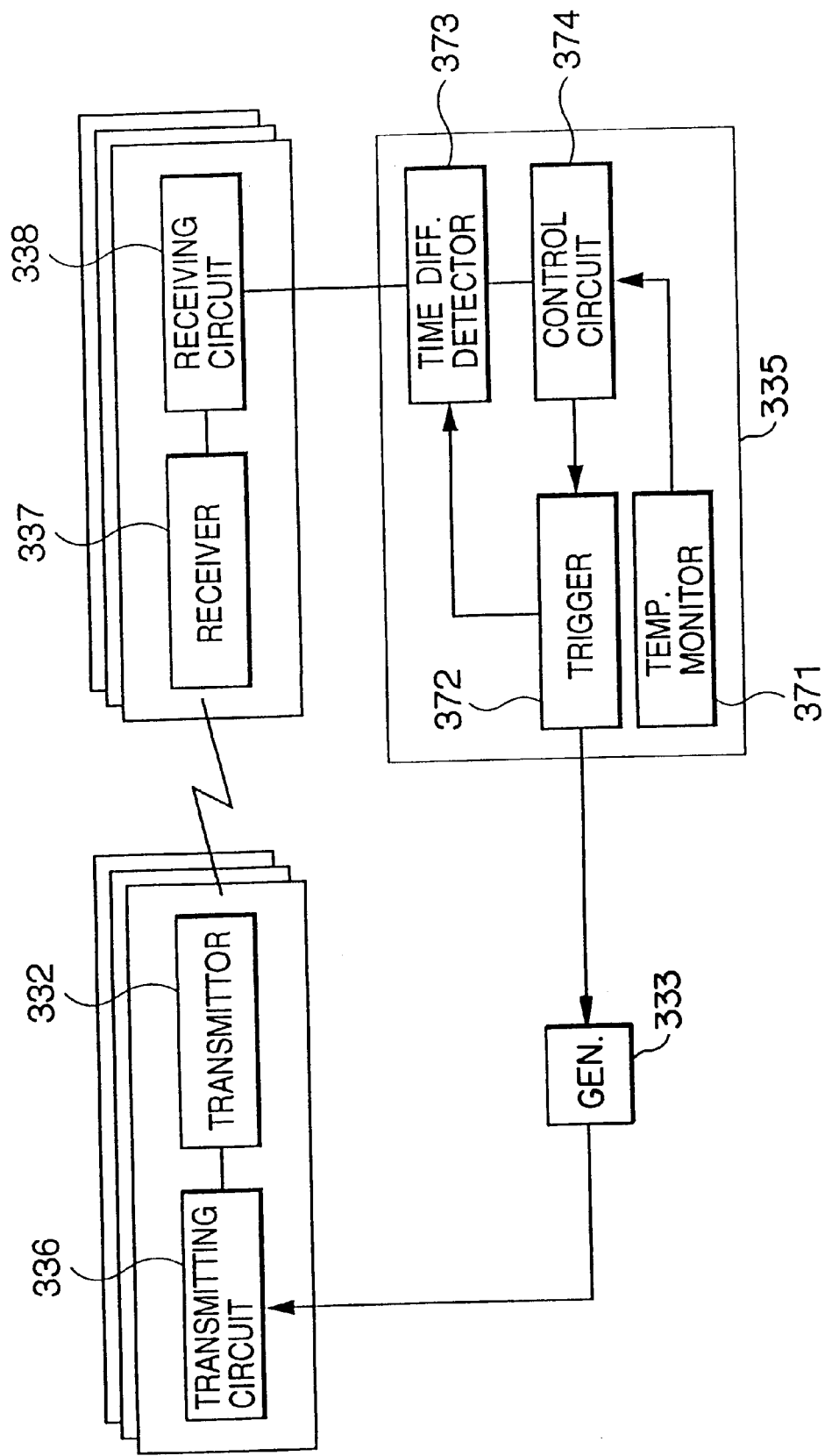
FIG. 35 is a block diagram showing this embodiment.

FIG. 35 shows a block diagram of the relative position measurement device 335.

To measure the ultrasonic propagation time accurately, the air temperature is measured by a temperature monitor 371 at the same time. By an instruction of a control circuit 374, a trigger circuit 372 generates a trigger signal. The trigger signal is sent to both the ultrasonic generator 333, which applies an ultrasonic signal to a transmission circuit 336, and to a time difference detection circuit 373. A receiver 337 receives ultrasonic waves propagating in air from a transmitter 332 and a receiving circuit 338 sends the received signal to the time difference detection circuit 373. By doing this, the obtained time difference data is collected by the control circuit 341. The relative position is calculated by the control circuit 374 or another calculator, such as computer 341.

Figure 36:
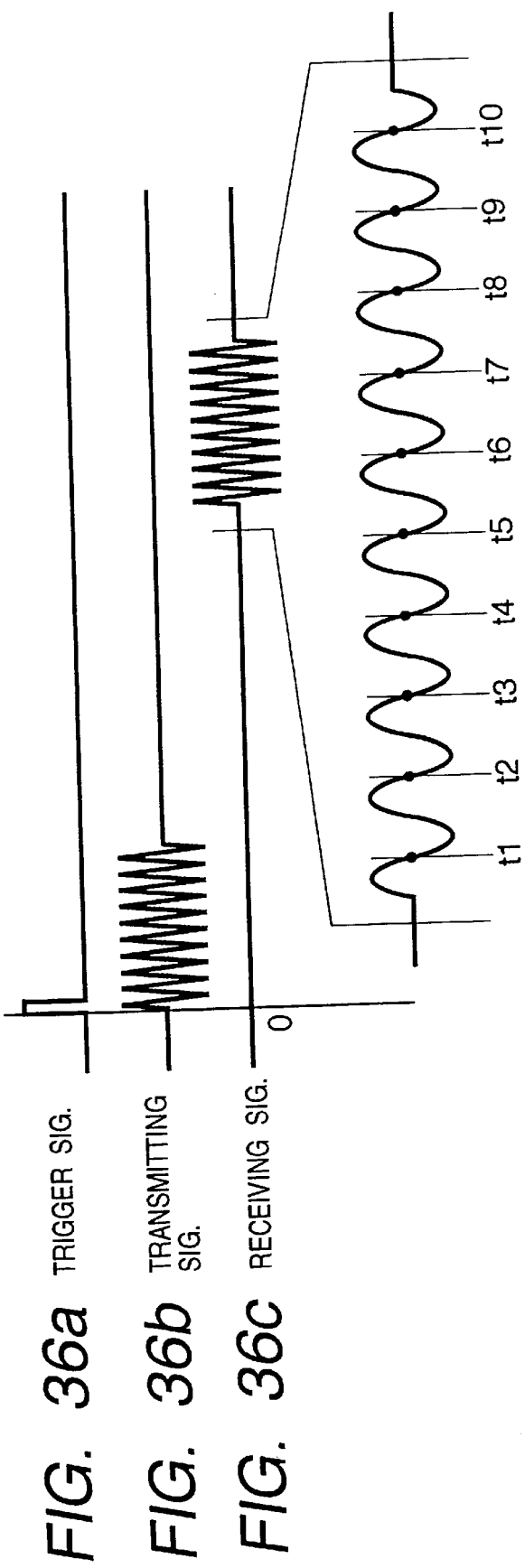
FIGS. 36a to 36c are signal diagrams for explaining the operation of this embodiment.

FIGS. 36a to 36c show signals for explaining the operation of this embodiment. To improve the accuracy of time difference detection, ultrasonic waves to be oscillated are set to a predetermined waveform. For example, a pattern including a repetition like a pulse used. The receiving side calculates the propagation time according to the oscillated waveform. For example, a train of ten pulses may be sent. The receiving side serves the pattern of pulses from the received signal and extracts time measuring points t1 to t10. When a mean value is obtained from this time data, the measurement error can be controlled more accurately than if the propagation time, for example, is obtained only from t1.

When the relative position measuring means is provided like this, the X-ray generator and X-ray detection device can be separated from each other. Since the apparatus is made smaller by doing this, the mobility increases. Namely, the apparatus can be brought to an imaging location on a narrow road or a location where piers are set close to each other and inspection can be carried out. The movement can be made faster and the inspection efficiency is improved.

When a third position reference device is provided as a relative position measuring means, in a location where the generator and detector are not visible from each other, that is, in the state wherein an inspection object is positioned between the two, the relative position can be measured and the apparatus can start radiography immediately. Radiography can be performed independently of the size and shape of the structure. Furthermore, for an inspection which involves moving the imaging location little by little, which is required for a large structure, radiography can be performed immediately without taking time for alignment for each movement. In this way, the inspection efficiency is improved and the apparatus can execute inspection of a large number of piers.

When three or more fixed measuring points are provided in the position reference device, three or more fixed measuring points in the X-ray generator, and three or more fixed measuring points in the X-ray detection device for relative position measurement, the positions of the X-ray generator and X-ray inspection apparatus can be accurately determined and the alignment accuracy is improved.

When arrival time measuring means using an ultrasonic pulse and measuring means for the air temperature at the measurement location are provided for distance measurement between measuring points, the accuracy of distance measurement can be improved further.

Furthermore, when means for generating a predetermined pattern signal and means for discriminating and detecting such a pattern signal are provided, the accuracy of distance measurement can be improved even further.

Furthermore, when generation means for generating a pattern signal several times and means for adding and averaging a received signal in synchronization with generation timing are provided, the accuracy of distance measurement can be improved still further.

When the distance measurement accuracy is improved, the alignment accuracy is also improved and an image of high resolution can be obtained. By doing this, detailed internal inspection is made possible and if a defect is found once, an efficient countermeasure can be taken.

Next, a non-destructive inspection apparatus which can specify a defect position in a large structure at high speed and an inspection method therefor will be explained.

For this purpose, a means for changing the position of the inspection object relative to the generator and the detection device without changing the relative position between the radiation generator and the radiation detection device, which are described above, is necessary.

The aforementioned radiation generator, in the same way as with the embodiments described above, is a means for generating radiation (X-rays, gamma rays, neutrons, etc.), such as an electron beam type accelerator or a cobalt 60 ray source.

The radiation detection device detects radiation generated from the radiation generator and sends it to a signal processing means as a current signal. Particularly, the radiation detection device in this embodiment has a characteristic structure as indicated below. Namely, a one-dimensional array of detectors in which a plurality of radiation detectors (scintillator detectors, semiconductor detectors, etc.) are arranged one-dimensionally are stacked up in 2 layers (this is called a two-layer radiation detector).

A means for changing the of the radiation generator and radiation detection device relative to position with an inspection object without changing the relative position between the radiation generator and the radiation detection device is provided as a means for moving the radiation generator and radiation detection device relative to the fixed inspection object perpendicularly to the arrangement direction of the one-dimensional array of detectors without changing the relative position between the radiation generator and the radiation detection device. Or, the means may comprise a means for moving the inspection object perpendicularly to the arrangement direction of the one-dimensional array of detectors relative to the fixed radiation generator and radiation detection device.

A signal processing means converts a radiation signal measured by the radiation detection device to a digital signal via a predetermined amplification process.

Furthermore, the apparatus has a storage means, which stores a digital signal received from the signal processing means and also stores analytical results produced by analytic means as well as various inspection parameters.

The analytic means converts a digital signal received from the signal processing means, which is stored in the storage means, to a form which is displayable by a display means and executes an analysis for specifying the defect position. The analytic means processes an input received via input means from an operator.

The display means displays the digital signal received from the signal processing means, which signal is converted by the analytic means, and also displays results analyzed by the analytic means. Furthermore, the display means also displays any input of data received from the input means.

This embodiment will be explained in more detail hereunder by referring to the drawings.

Figure 37:
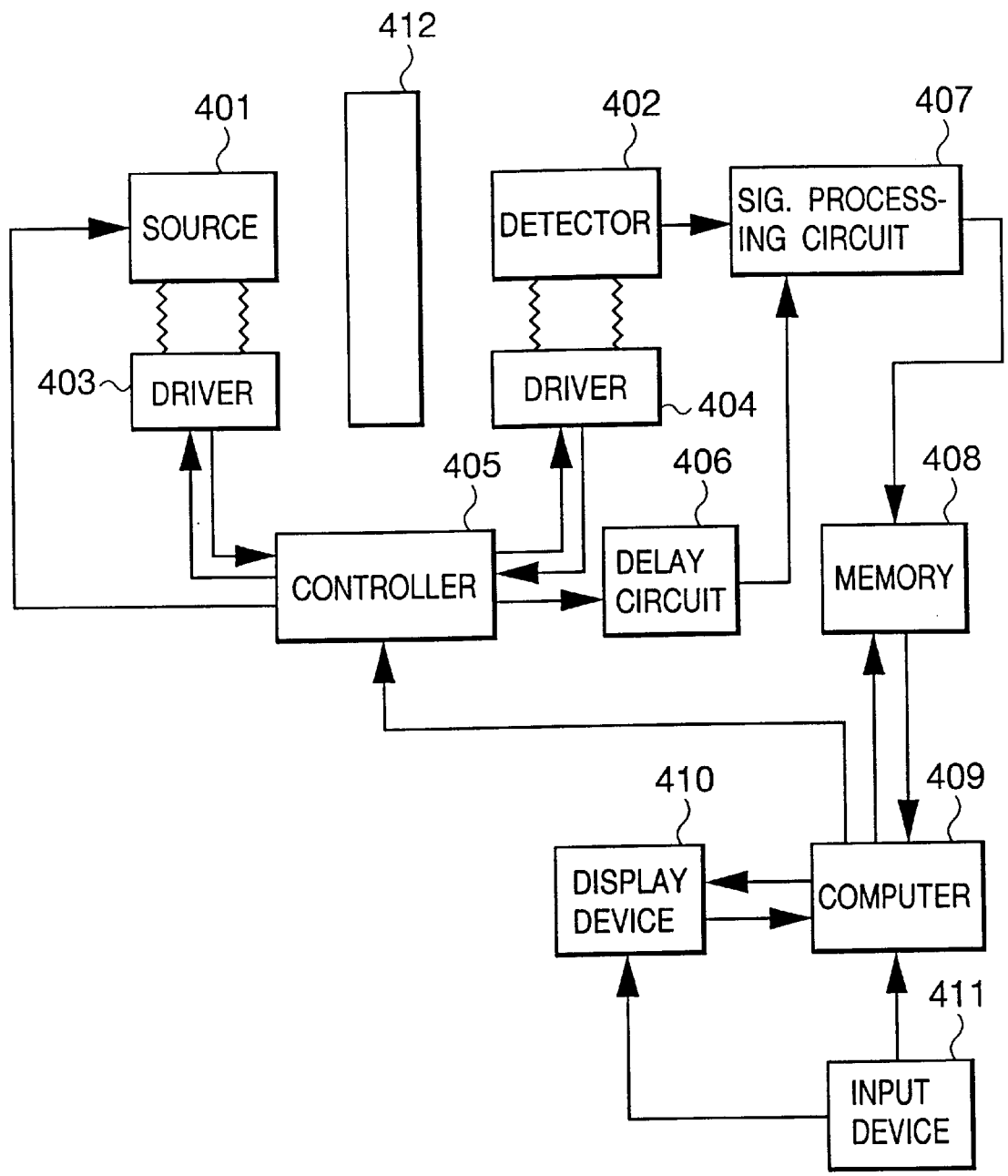
FIG. 37 is a block diagram showing the constitution of a non-destructive inspection apparatus using radiation.

FIG. 37 shows the constitution of the non-destructive inspection apparatus of this embodiment. The inspection apparatus comprises a radiation source 401, a multi-channel radiation detector 402, a radiation source driver 403, a radiation detector driver 404, a drive controller 405, a delay circuit 406, a radiation signal processing circuit 407, a memory 408, a computer 409, a display device 410, and an input device 411. An inspection object 411 is positioned and fixed between the radiation source 401 and the multi-channel radiation detector 402. These various components will be described hereunder in detail.

Figure 53:
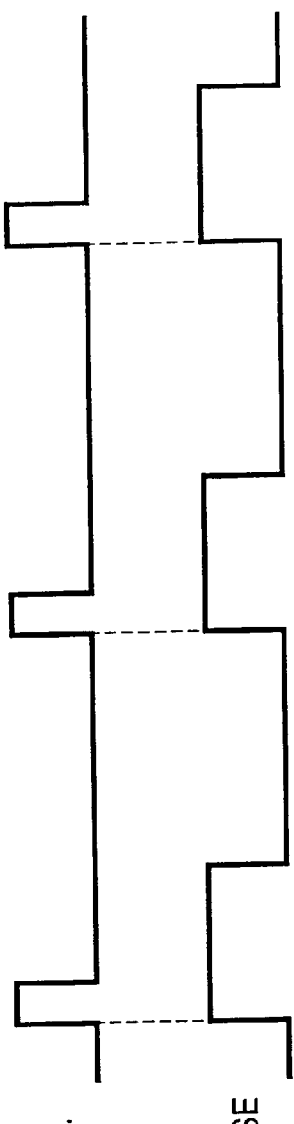
FIGS. 53a and 53b are signal diagrams forming a time chart of a trigger signal and an X-ray pulse.

In the embodiment shown in FIG. 37, the radiation source 401 is an electron beam accelerator. The electron beam accelerator functions as an X-ray generator. Generation of X-rays is started by an external trigger signal and X-rays are generated whenever this trigger signal is inputted. Generated X-rays are, for example, something like a pulse having a time length of 5 micro seconds. The timing of a trigger signal and an X-ray pulse are shown in FIG. 53a and FIG. 53b.

The structure of the multi-channel radiation detector 402 in the embodiment shown in FIG. 37 will be explained by referring to the drawings.

Figure 38:
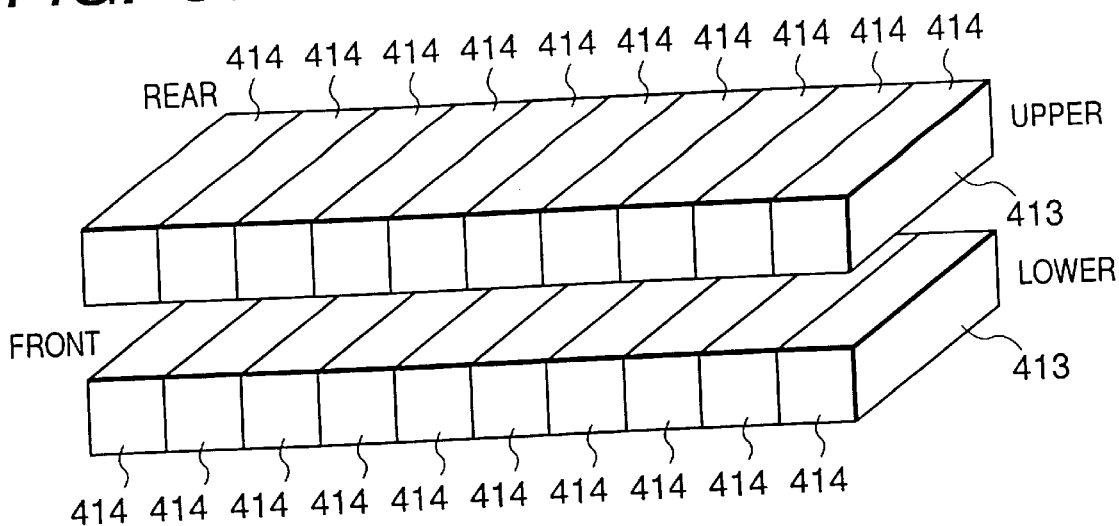
FIG. 38 is a diagram of a multi-channel radiation detector used in the aforementioned apparatus.

The multi-channel radiation detector 402 in the embodiment is one-dimensional array of detectors 413 stacked up in 2 layers, as shown in FIG. 38. The one-dimensional array of detectors 413 is made up of a plurality of radiation detectors 414 (scintillator detectors or semiconductor detectors) which are arranged one-dimensionally and each radiation detector 414 constituting the one-dimensional array of detectors 413 is arranged so as to face the radiation source 401 (point source) at a certain distance from the front of the detector.

Figure 39:
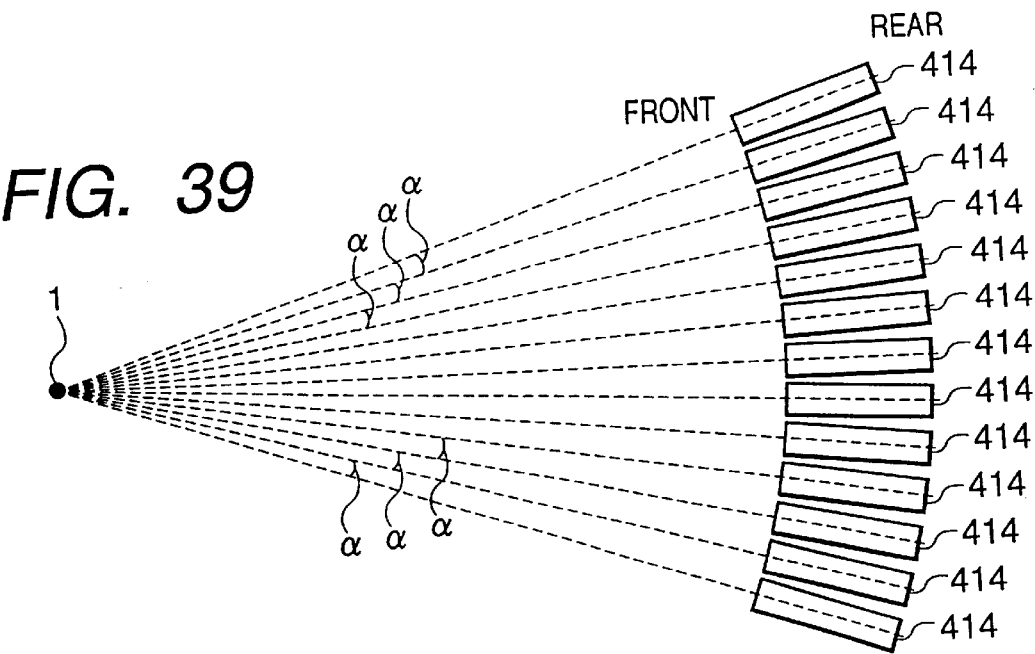
FIG. 39 is a diagram of the multi-channel radiation detector shown in FIG. 38 as viewed from above.

To indicate this situation, the multi-channel radiation detector 402 shown in FIG. 38 is shown in FIG. 39 as seen from above. In FIG. 39, it can be seen that the front of the one-dimensional array of detectors 413 is curved. However, it also may be arranged in a straight line. In this embodiment, the angle between each radiation detector 414 constituting the one-dimensional array of detectors 413 is an equal angle ($\alpha$). The angle between the radiation detectors 414 is a parameter necessary to specify the internal defect position of the inspection object 412. The arrangement of these one-dimensional arrays of detectors 413 is decided correctly during production of the detectors and each radiation detector 414 constituting a one-dimensional array of detectors 413 is fixed so as to be preserved semi-permanently. By doing this, a fan-shaped radiation beam from the radiation source can be detected efficiently.

Figure 40:
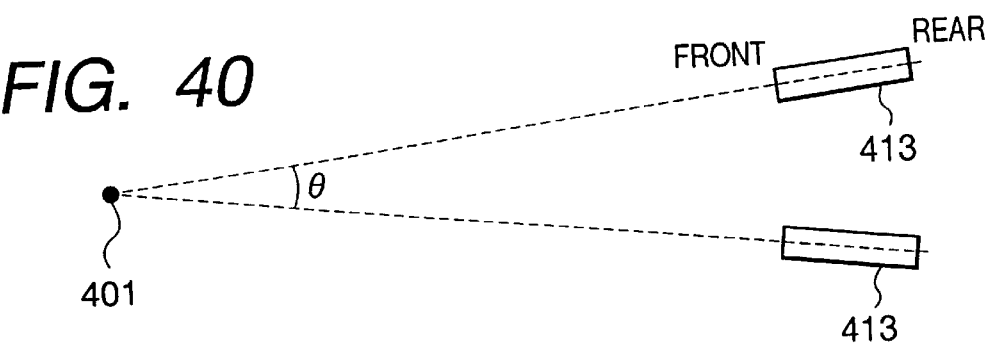
FIG. 40 is a diagram of the multi-channel radiation detector shown in FIG. 38 as viewed from the side.

The multi-channel radiation detector 402 shown in FIG. 38 is shown in FIG. 40 as seen from the side. The angle between the one-dimensional array of detectors 413 in the upper row and the one-dimensional array of detectors 413 in the lower row facing the radiation source 401 respectively is taken as $\theta$. This angle $\theta$ is a parameter necessary to specify the internal defect position of the inspection object 412, so that the angle $\theta$ is determined correctly during production of the detectors and the one-dimensional array of detectors 413 in the upper and lower rows are fixed and installed so as to be preserved semi-permanently. Each radiation detector 414 constituting the one-dimensional array of detectors 413 in the upper and lower rows is wired so as to send a radiation detection signal (current signal) to the signal processing circuit 407.

Figure 51:
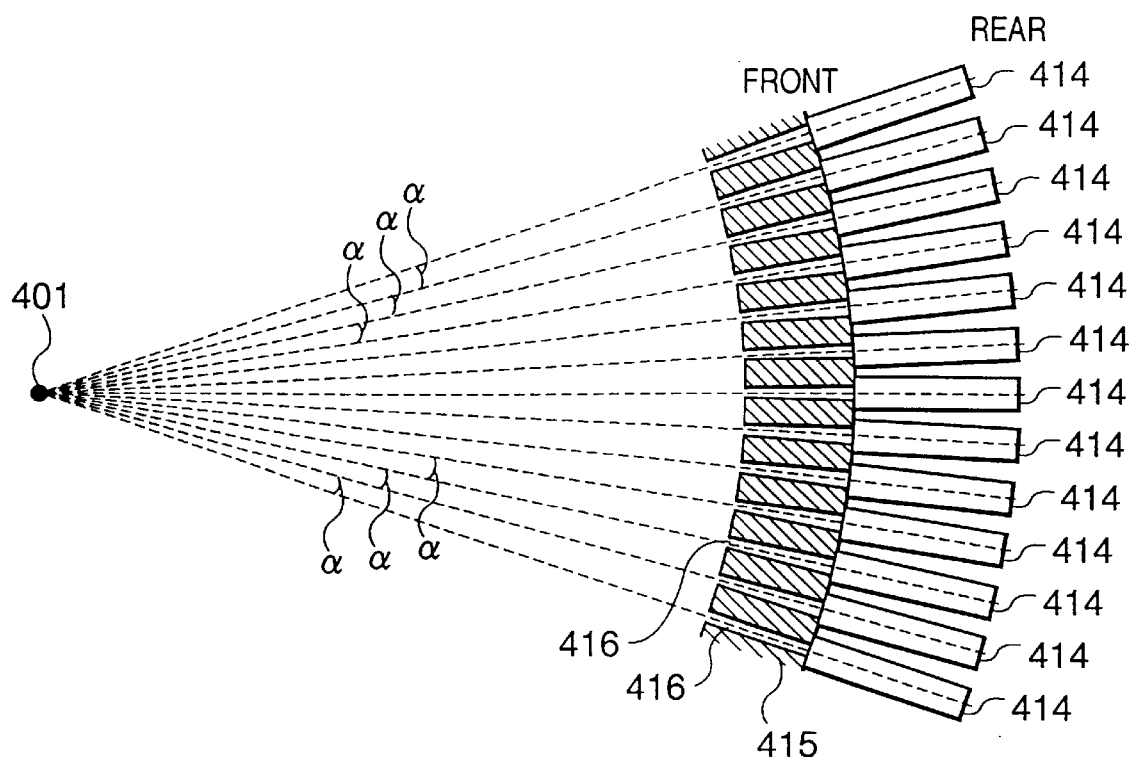
FIG. 51 is a sectional view showing a deformation example of a multi-channel radiation detector.

An example of a variation of the aforementioned multi-channel radiation detector 402 will be explained by referring to FIG. 51. In this example, in the one-dimensional array of detectors 413 constituting the multi-channel radiation detector 402, a collimator 415 is installed in front of each radiation detector 414 constituting the one-dimensional array of detectors 413. In each collimator 415, a respective slit 418 corresponds to each radiation detector 414. These collimators 415 are made of a material suited to the shielding of radiation, such as lead or tungsten. These collimators 415 prevent radiation scattered by the inspection object 412 from entering the radiation detectors 414, so that the quality of a transmission image can be improved.

Figure 52:
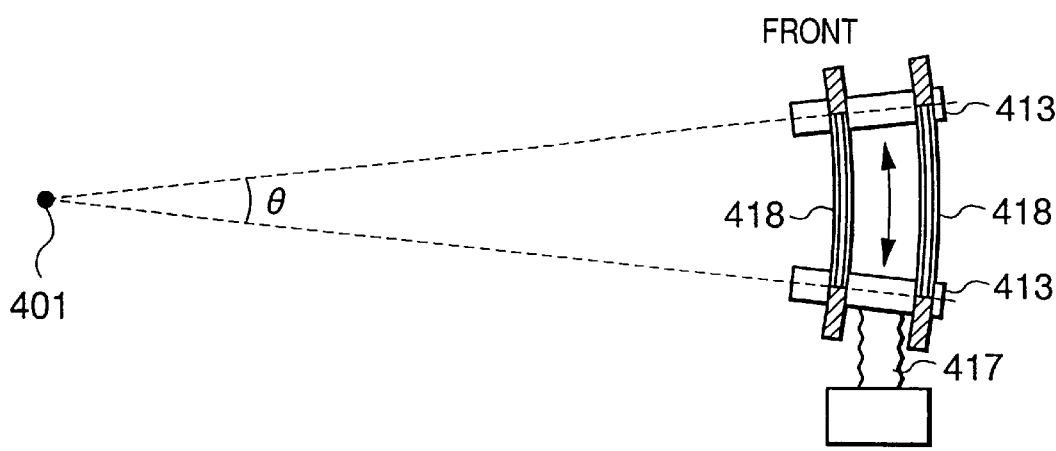
FIG. 52 is a diagram showing a deformation example of a multi-channel radiation detector.

Another example of a variation of the aforementioned multi-channel radiation detector 402 is shown in FIG. 52. In this example, the one-dimensional array of detectors 413 are not stacked up in two layers, but are arranged only in one layer. However, a detector array moving device 417 for moving a one-dimensional array of detectors 413, when positioned in the lower row, to the upper row, and the same one-dimensional array of detectors 413, when positioned in the upper row, to the lower row, is additionally installed.

The one-dimensional array of detectors 413 move along rails 418 and using the rails 418, the one-dimensional array of detectors 413 can be positioned automatically. When a one-dimensional array of detectors is used, detectors having a higher sensitivity than that of a two-dimensional array of detectors can be obtained easily, so that a transmission image produced by a cone beam can be obtained at high speed. When a two-layer constitution is used as shown in FIG. 38, the aforementioned transmission image can be obtained in two directions at the same time, so that the radiography can be speeded up even more. Particularly, in the case of two layers, only one scan is required compared with the case of one layer, so that the radiography can be speeded up.

The structures of the radiation source driver 403 and the detector driver 404 in the embodiment shown in FIG. 37 will be explained hereunder. Since these drivers have the same structure and function, the radiation source driver 403 will be used for explanation.

Figure 41:
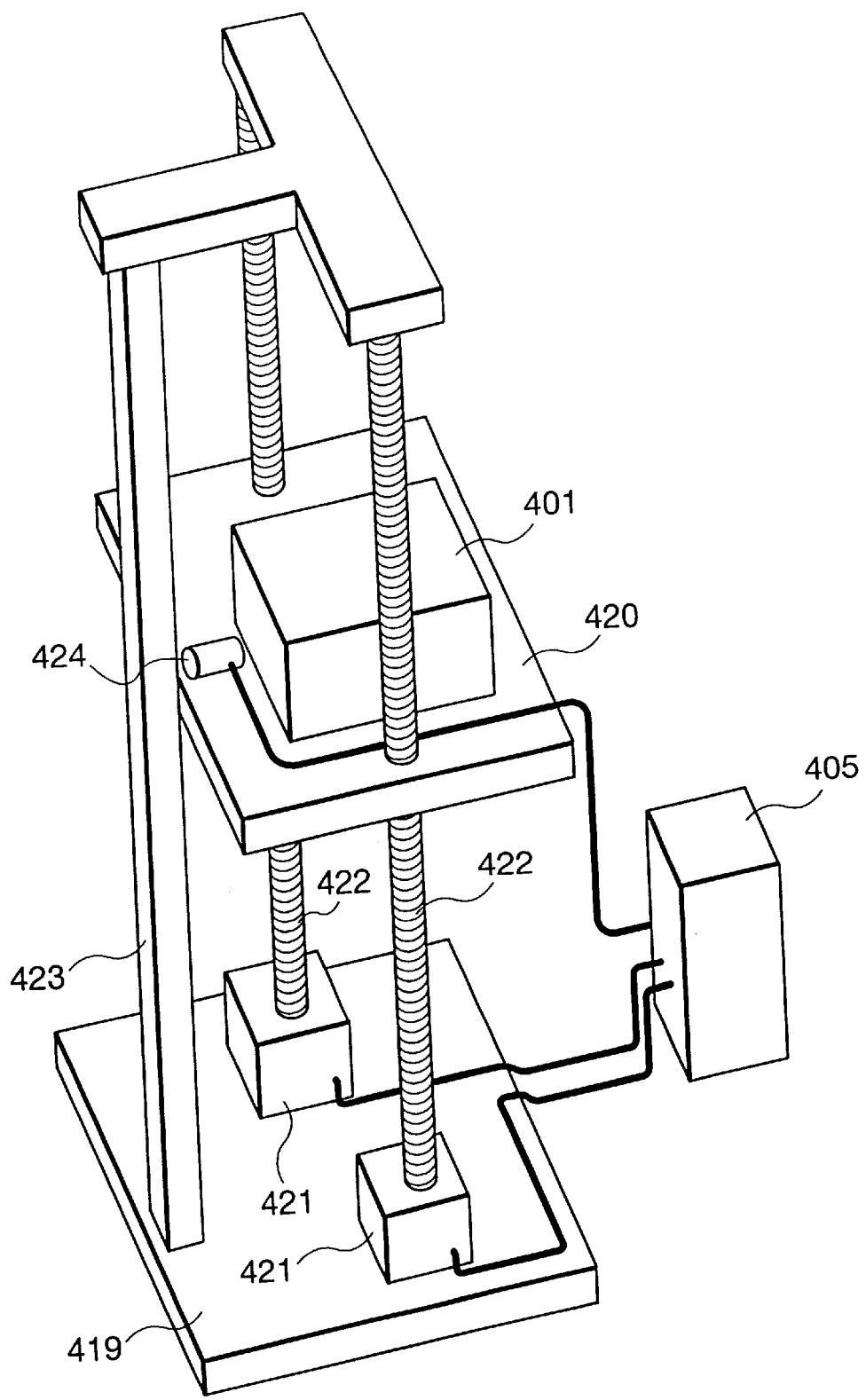
FIG. 41 is a structural diagram of a radiation source driver.

The structure of the radiation source driver 403 is shown in FIG. 41. The radiation source driver 403 has a fixing stand 419 for fixing and installing the driver and a movable stand 420 moving the radiation source up and down. The radiation source 401 is fixed and installed on the movable stand 420. The movable stand 420 is moved by a drive shaft 422 which is rotated by a motor 421 installed on the fixing stand 419. The rotation of the motor is controlled by the drive controller 405. This driver has a scale 423 and a scale reader 424 (fixed and installed on the movable stand 420) so as to facilitate positioning in response to a signal from the scale reader 424, which signal is sent to the drive controller 405.

In this embodiment, the scale 423 is a tape on which a magnetic signal is recorded every 0.1 mm and the scale reader 424 has a magnetic head (a magnetic scale is a general term for the scale and scale reader). Signals from the magnetic scale are a signal showing the direction of vertical movement and a pulse signal generated every 0.1 mm.

The function of the drive controller 405 in the embodiment shown in FIG. 37 will be explained.

The function of the drive controller 405 is determined by an instruction received from the computer 409. Namely, an initial position (height) of the radiation source 401, initial position (height) of the multi-channel radiation detector 402, moving direction, moving speed, sampling interval, sampling size, and start signal are sent to the drive controller 405 from the computer 409. These parameters are inputted to the computer 409 by an operator using the input device 411. To eliminate inconvenience of a repetitive input of this data, it is possible to store this information the memory 408.

The drive controller 405 controls the motor 421 so as to move the radiation source 401 and the multi-channel radiation detector 402 to their initial positions. Upon receipt of the start signal from the computer 409, the drive controller 405 starts the motor 421 so as to move the radiation source 401 and the multi-channel radiation detector 402 according to the set moving speed immediately. Both for acceleration and deceleration, it is necessary that the moving speed of the radiation source 401 is equal to that of the multi-channel radiation detector 402.

While the radiation source 401 and the multi-channel radiation detector 402 are moving, position signals are sent to the drive controller 405 from the scale reader 424 and the drive controller 405 receiving these position signals sends a sampling signal to the radiation source 401 and the delay circuit 406 in the set sampling intervals. When the set sampling size is reached, the drive controller 405 controls the motor 421 so as to stop the movement.

Figure 42:
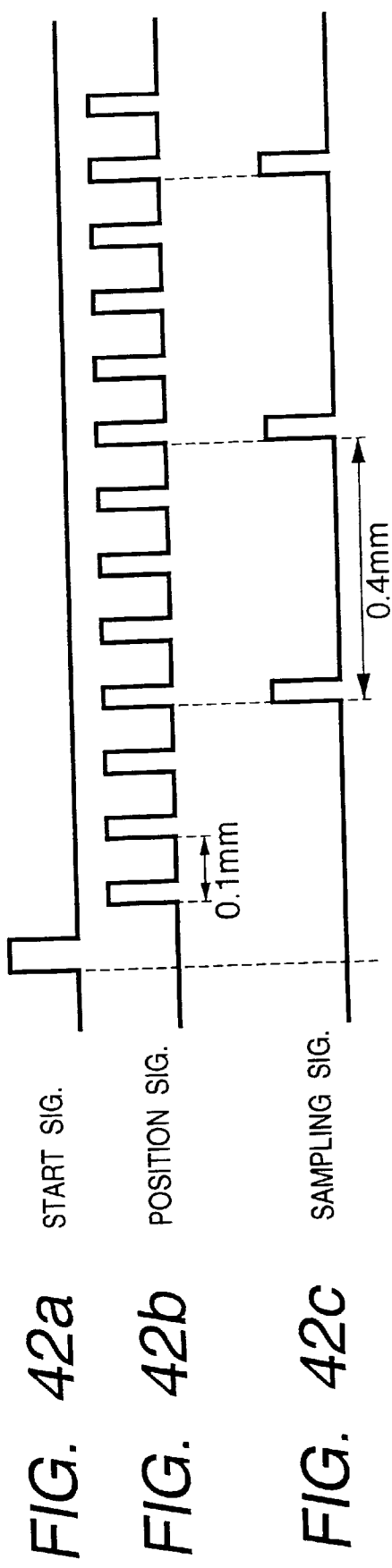
FIGS. 42a to 42c are signal diagrams forming a time chart of a start signal, position signal, and sampling signal.

FIGS. 42a to 42c show the timing of the start signal, position signal, and sampling signal. As seen in the drawings, the moving speed of the movable stand 420 is almost at a uniform velocity and a scale reading signal is generated at an interval of 0.1 mm. The sampling interval is 0.4 mm.

The functions of the multi-channel radiation detector 402, the delay circuit 406, the signal processing circuit 407, and the memory 408 in the embodiment shown in FIG. 37 will be explained hereunder.

In the one-dimensional array of detectors 413 constituting the multi-channel radiation detector 402, the radiation detectors 414 constituting the one-dimensional array of detectors 413 are silicon semiconductor detectors particularly as a solid detector. A radiation signal is converted from Upon receipt of a sampling signal from the drive controller 405, the radiation source 401 generates radiation. Namely, a sampling signal sent to the radiation source 401 from the drive controller 405 is viewed as a trigger signal from the side of the radiation source 401. Generated X-rays are produced in the form of a pulse having a certain time length, and the generation direction is toward the multi-channel radiation detector 402 from the radiation source 401, and X-rays are almost unidirectional within a certain angle range in the radiation direction.

Generated X-rays pass through the inspection object 412 and enter the radiation detectors 414 of the one-dimensional array of detectors 413 constituting the multi-channel detector 402, and the radiation detectors 414 generate a current signal in proportion to the intensity of incident X-rays. The signal processing circuit 407 converts the generated current signal to a voltage signal (called a detector output voltage).

Figure 43:
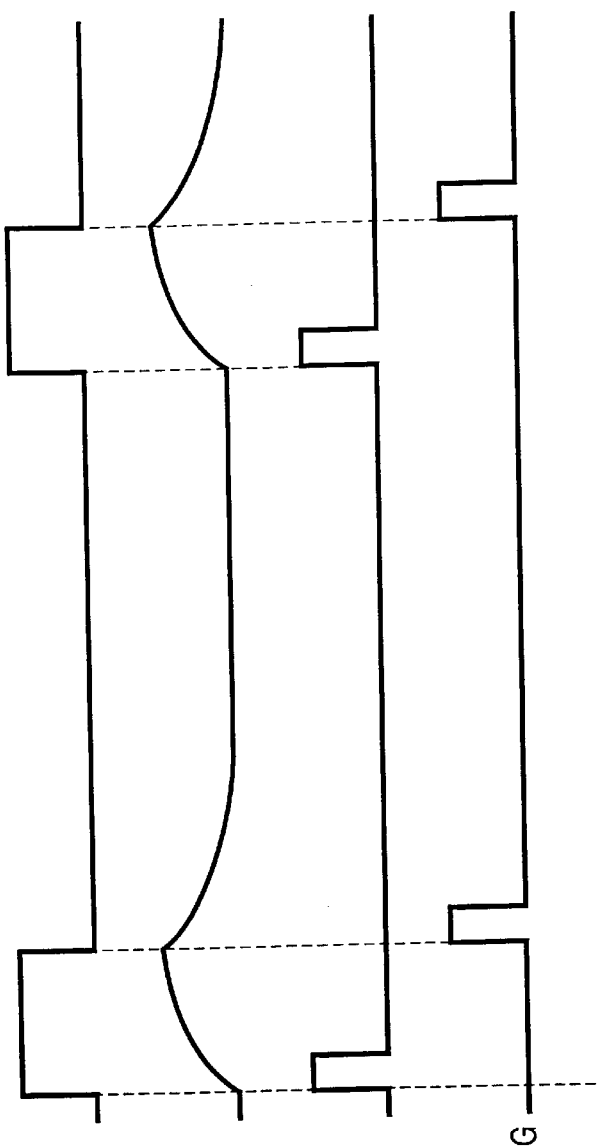
FIGS. 43a to 43d are signal diagrams forming a time chart of signal processing.

The X-ray pulse and detector output voltage are as shown in FIGS. 43a and 43b. The voltage signal has a peak and this peak voltage is a detection signal, so that a sample hold element within the signal processing circuit 407 holds the peak voltage. To execute this sample hold, a sample hold start signal is necessary.

This signal is generated by the delay circuit 406 using the following procedure. Namely, a signal which is the same as the sampling signal sent to the radiation source 401 is sent to the delay circuit 406 from the drive controller 405 (FIG. 43c). Upon receipt of this sampling signal, the delay circuit 406 outputs a signal after a suitable time lag (FIG. 43d).

The output signal from the delay circuit 406 is received by the sample hold element and is changed to a sample hold start signal, so that it is called a sample hold signal. This sample hold signal is subjected to time lag adjustment so that the detector output voltage is maximized (this adjustment is executed during apparatus production and is not required during inspection). This series of current-voltage conversion and sampling hold operations are structured so as to have a one-to-one correspondence with all the radiation detectors 414 constituting the multi-channel radiation detector 402. In brief, when the total number of radiation detectors 414 is 100, the numbers of current-voltage conversion elements and sample hold elements are also 100, respectively.

The voltage signal held by the sample hold elements is converted to a digital signal by an analog-digital converter (called a detector output signal). The detector output signal is stored by the memory 408. The storing address is determined uniquely from the sampling number and the number of the radiation detector 414. For example, assuming that the sampling number is k (the sampling number starts with 0), and the number n of radiation detectors 414 constituting the one-dimensional detectors 413 in the upper row is 0 to (N−1), and the number n of radiation detectors 414 constituting the one-dimensional detectors 413 in the lower row is N to (2N−1), the address where the output of the detector number n is stored is (n+2N×(k−1)).

The functions of the computer 409, the display device 410, and the input device 411 in the embodiment shown in FIG. 37 will be explained hereunder.

The computer 409 reads the detector output signal stored in the memory 408, divides it into detector output signals detected by the one-dimensional array detectors 413 in the upper row and detector output signals detected by the one-dimensional array detectors 413 in the lower row, and displays them on the display device 410 as two images. This is realized as shown below.

For example, it is assumed that the inspection object 412 is a concrete column 425 which is 10 cm in diameter, and has an inner spherical hole 426 which is 5 cm in diameter. The hole 426 is positioned at the inner center of the column 425 and at a height of 1 m from the bottom of the column 425. The inspection object 412 is positioned between the radiation source 401 and the multi-channel radiation detector 402 and the radiation source 401 and the multi-channel radiation detector 402 move vertically upward along the column. The moving direction is perpendicular to the direction of the one-dimensional array of detectors 413.

Figure 44:
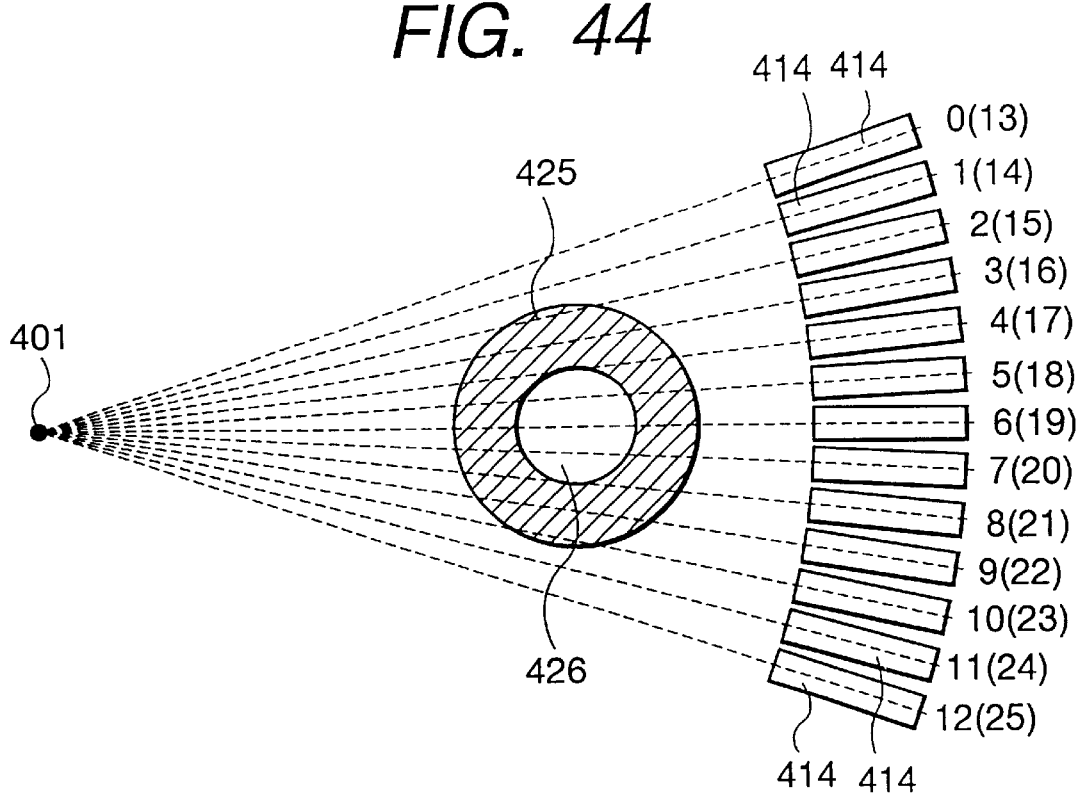
FIG. 44 is a plan view showing the positional relationship of a radiation source, multi-channel radiation detector, and inspection object.
Figure 45:
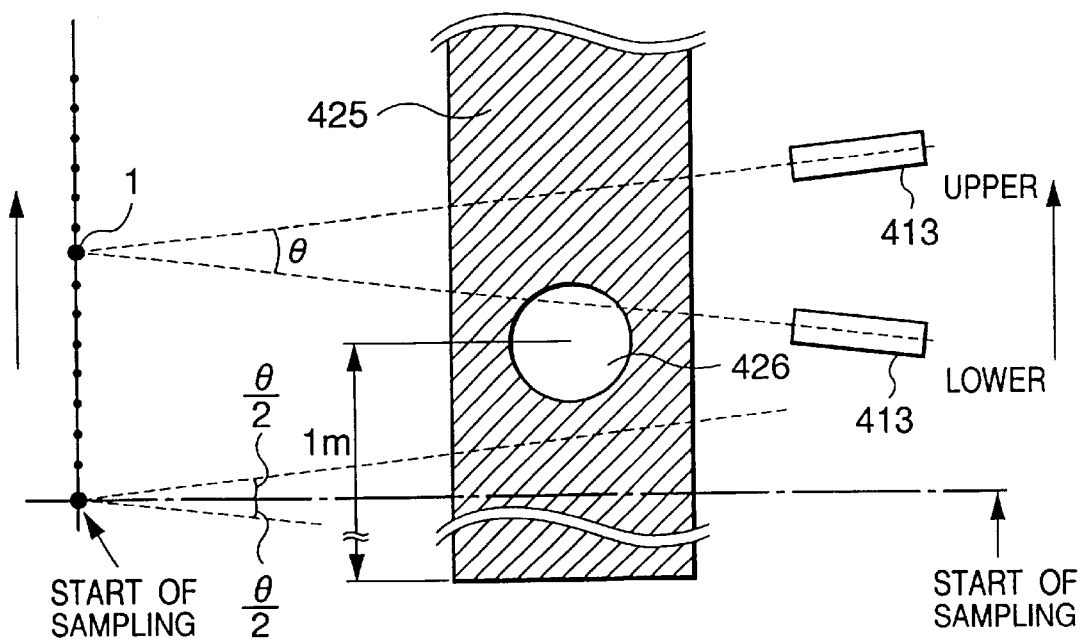
FIG. 45 is a side view showing the positional relationship of a radiation source, multi-channel radiation detector, and inspection object.

This situation as viewed from above is shown in FIG. 44 and the situation as viewed from the side is shown in FIG. 45. It is assumed that the radiation detectors 414 constituting the one-dimensional array of detectors 413 in the upper row are numbered 0 to (N−1) and the radiation detectors 414 constituting the one-dimensional array of detectors 413 in the lower row are numbered N to (2N−1) (an example of numbering when N=13 is shown in FIG. 44, and the numbers without ( ) are the numbers of the detectors in the upper row, and the numbers with ( ) are the numbers of the detectors in the lower row).

Figure 48:
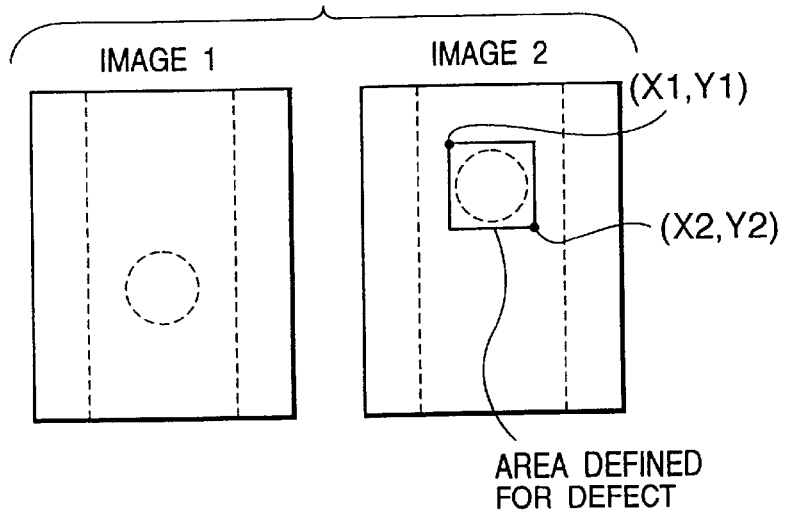
FIG. 48 is a diagram showing region designation of a defective portion.

It is assumed that the sampling size is between o and (K−1) and the sampling interval is Δ. It is assumed that the sampling start position SS is the location where the line connecting the one-dimensional array of detectors 413 in the upper row and the radiation source 401 is positioned under the hole 426 and the sampling end position is the location where the line connecting the one-dimensional array of detectors 413 in the lower row and the radiation source 401 is positioned above the hole 426. Under such a condition, two images are formed as shown in FIG. 48, for example.

The computer 409 reserves two two-dimensional image memories with a size of N×K for two images. These are designated as a memory for image 1 and a memory for image 2 for convenience. It is assumed that the memory for image 1 is used for the one-dimensional array of detectors in the lower row and the memory for image 2 is used for the one-dimensional array of detectors in the upper row. The computer 409 reads the detector output signals stored in the memory 408 sequentially starting with address 0 (it is assumed that the detector output signals are addressed by the method explained as an example before). The computer 409 stores the read data in the image memory according to the following procedure.

Figure 46:
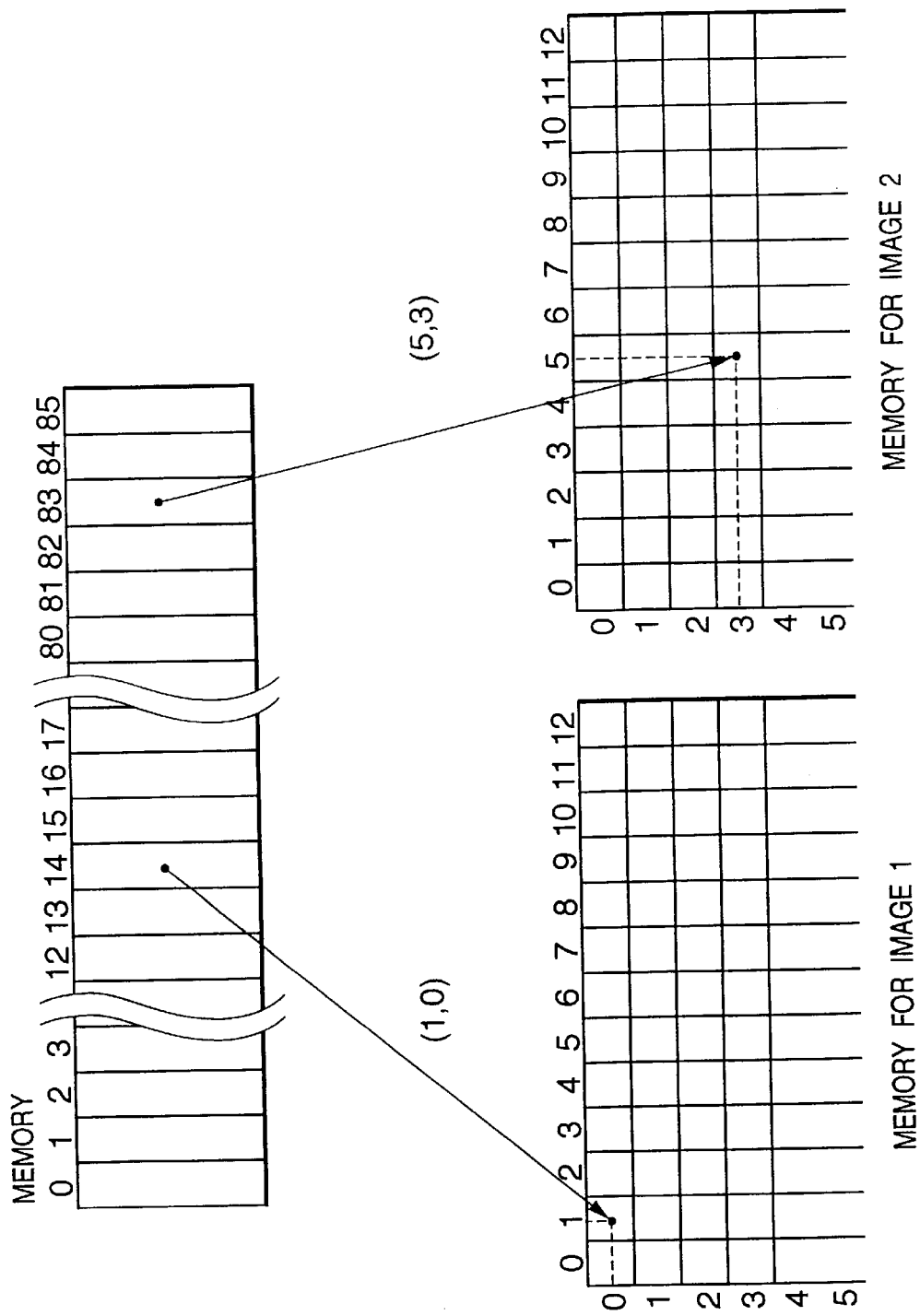
FIG. 46 is a diagram showing an imaging method.
Figure 47:
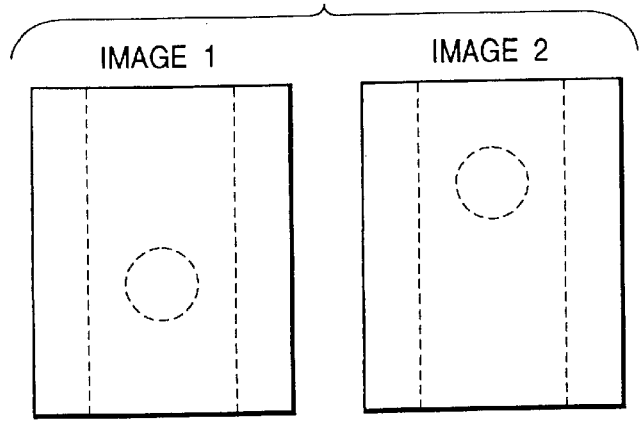
FIG. 47 is a drawing showing a transmission image displayed on the display unit.

Namely, it is assumed that the quotient when the address is divided by N is n and the remainder is m. It is also assumed that the quotient when the address is divided by 2N is k. Firstly, when n is an odd number, the memory for image 1 is selected and the read signal is stored in the location indicated by (m, k). When n is an even number, the memory for image 2 is selected and the read signal is stored in the location indicated by (m, k). This situation is shown in FIG. 46. When all the data is read from the memory 408, the images shown in FIG. 47 can be displayed on the display device 410. The image 1 corresponds to the memory for image 1 and the image 2 corresponds to the memory for image 2. An operator cannot see the memory for image 1 and the memory for image 2 directly but can see the image 2 and the image 2.

Next, the defect position specifying method will be explained. In this embodiment, in FIGS. 44 to 47, the spherical hole 426 in the concrete is regarded as a defect for purposes of explanation.

An operator can see the image 1 and image 2 shown on the display device 410. The area of the defect is designated in one of the image 1 and image 2. For this embodiment, a method of clearly indicating by an operator the extraction of a defect will be explained in detail. However, for extraction of a defect, automatic recognition by a computer is also possible. Actually, many methods, such as the template matching method or a method using a neural network, have been designed. For example, in the image 1 and image 2 shown in FIG. 47, the operator designates the area of a defect for the image 2 (FIG. 48).

Next, a method of designating the area of a defect will be described. Firstly, it is assumed that the shape of an area to be designated has been determined. For example, the area is assumed to be a quadrangle or a circle. In the case of a quadrangle, an operator designates the two points representing the upper left corner and the lower right corner in the computer using the input device. In the case of a circle, he designates the center position and radius using the input device. The computer displays the inputted area on the display device. FIG. 48 shows the display produced by the display device 410 when the shape of the area is a quadrangle. The operator decides whether the area displayed on the display device 410 is satisfactory. If it is not acceptable, the operator designates the area once again. If it is acceptable, the operator inputs a response indicating no change of the area by way of the input device.

Upon receipt of the input no change of the area, the computer 409 executes the following process internally. Namely, the area designated by the image 2 is determined from the position of the upper left corner (X1, Y1) and the position of the lower right corner (X2, Y2) in FIG. 48. The computer 409 copies this designated area in the fixed area memory. Next, the computer 409 copies the area designated by the position of the upper left corner (X1, Y1) and the position of the lower right corner (X2, Y2) in the image 1 (this is not the image in which the area is designated) into the variation area memory. Next, the computer 409 calculates the correlation coefficient between the contents of the fixed area memory and the contents of the variation area memory. when the computer 409 calculates the correlation coefficient, the computer 409 stores it in the correlation coefficient memory. Next, the computer 409 copies the area designated by the position of the upper left corner (X1, Y1+1) and the position of the lower right corner (X2, Y2+1) of the image 1 into the variation area memory. The computer 409 calculates the correlation coefficient between the contents of the fixed area memory and the contents of the variation area memory and copies the correlation coefficient in the correlation coefficient memory. The computer 409 continues this operation until the position of the lower right corner reaches the bottom of the image 1.

When this series of operations ends, the computer 409 detects the maximum value of the correlation coefficient, displays the variation area when the maximum value is obtained on the image 1, and calculates the movement distance D expressing the movement distance of the variation area from the initial position. In this case, the operator decides whether this variation area is the desired area or not on the basis of the display of the image 1. When it is the desired area, it may be designed to calculate the movement distance D.

Figure 49:
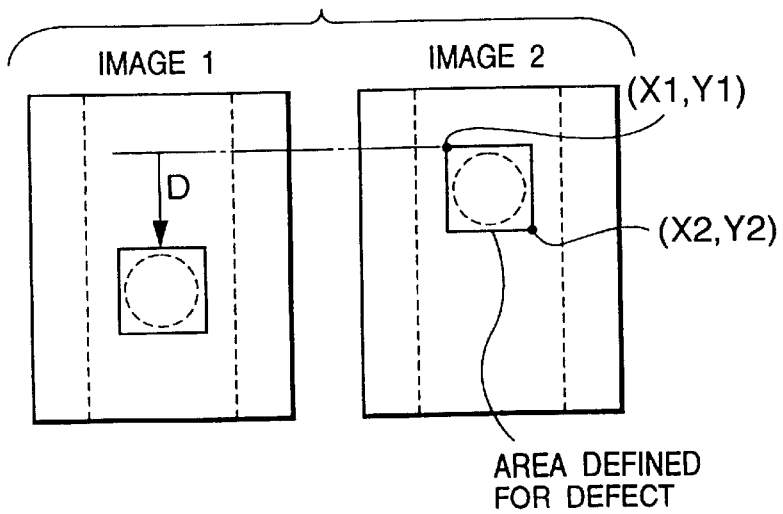
FIG. 49 is a diagram showing the position of a region whose coefficient of correlation reaches the maximum value.

FIG. 49 shows the situation when the position of the variable area when the correlation coefficient is maximized is displayed on the display device 410 and also displays the movement distance D.

The computer 409 calculates the distance L of the defect from the radiation source using the following formula obtained from the movement distance D, the sampling interval A, and the angle θ between the one-dimensional array of detectors 413 in the upper row and the one-dimensional array of detectors 413 in the lower row:

$$L = \frac{\Delta \cdot D}{2 \cdot \tan\left(\frac{\theta}{2}\right)} \quad (1)$$

The computer 409 calculates the height of the defect position H using the following formula obtained from the sampling start position SS, the sampling interval Δ, Y1 and Y2 inputted by area designation of the defect position:

$$H = SS + \Delta \cdot \frac{Y1 + Y2}{2} \quad (2)$$

The value of H is calculated as a coordinate of the scale 423.

Furthermore, the computer 409 calculates the position T of the defect in the horizontal direction using the following formula obtained from the angle alpha between the radiation detectors 414 constituting the one-dimensional array of detectors 413 in the upper row and X1 and X2 inputted by area designation of the defect position:

$$T = \frac{X1 + X2}{2} \cdot \alpha \quad (3)$$

The value of T is expressed by an angle. Information as to the calculated defect positions is displayed on the display device 410.

Figure 50:
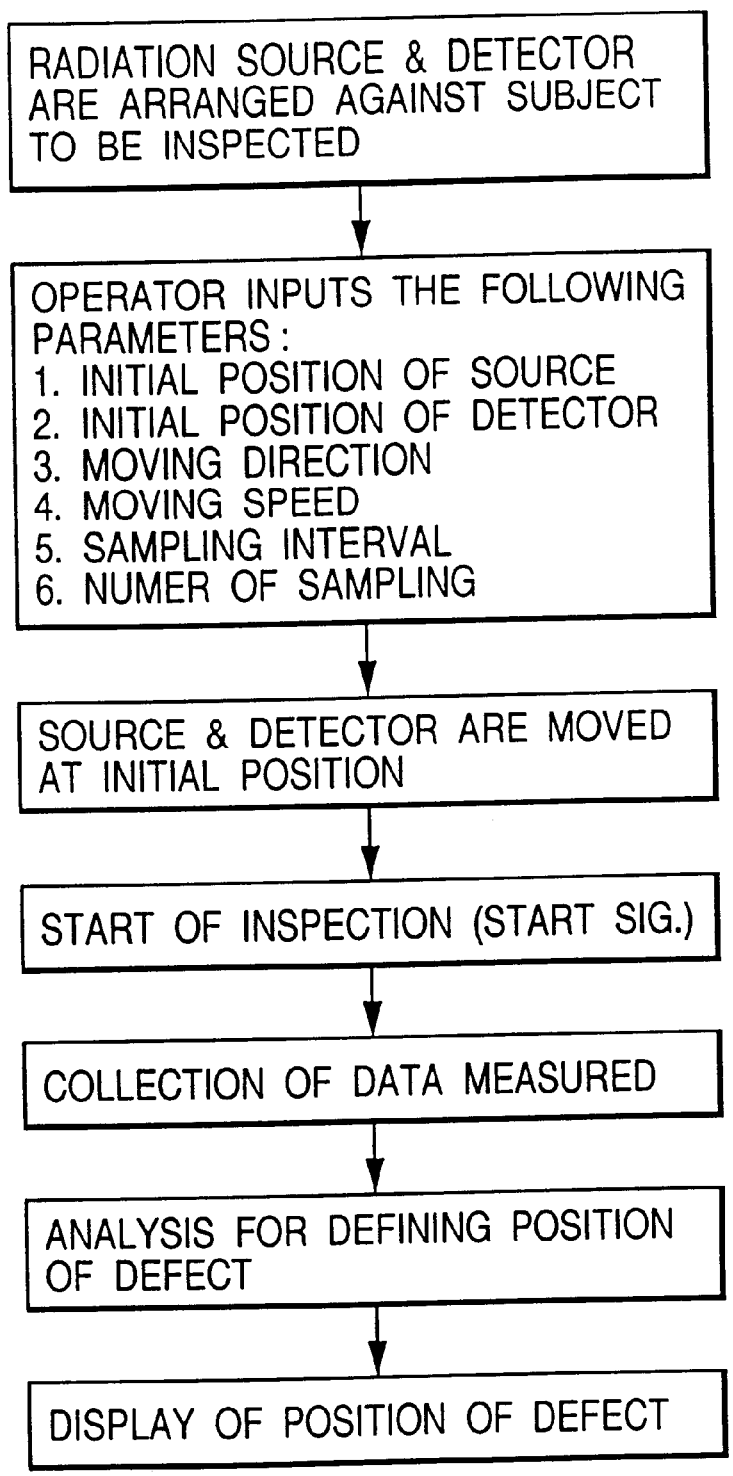
FIG. 50 is a flow chart of inspection using a radiation inspection apparatus.

FIG. 50 shows a flow chart of the inspection process using this non-destructive inspection apparatus. Firstly, the radiation source 401 and the multi-channel radiation detector 402 are installed on both sides of the inspection object 412. In this case, the multi-channel radiation detector 402 determines the position so that the radiation detector 402 is an alignment with the radiation source 401 correctly.

Next the parameters necessary for inspection are inputted by the operator from the input device 411. The parameters to be inputted are the initial position of the radiation source 401, initial position of the multi-channel radiation detector 402, moving direction, moving speed, sampling interval, and sampling size. The inputted parameters are sent to the drive controller 405 from the computer 409, and the radiation source 401 and the multi-channel radiation detector 402 are moved to the initial positions, and the preparation for inspection is completed.

The inspection starts when the operator inputs the start signal to the computer 409. When the inspection starts, the apparatus collects a series of measured data and then the operator and computer go to analyzing and specifying the defect position interactively. Finally, the computer 409 displays the defect position and the inspection operation ends.

Figure 54:
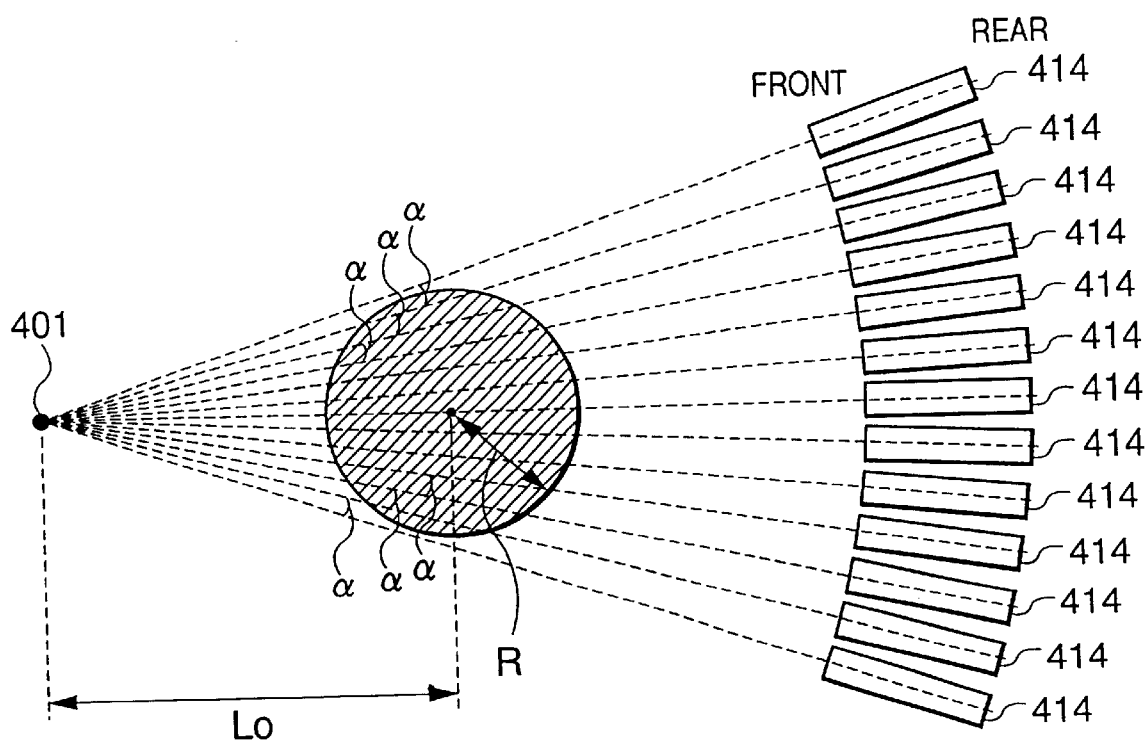
FIG. 54 is a plan view for explaining apparatus parameters.

Actual numerical values of alpha, theta, and delta which are important parameters will be explained by referring to FIG. 54.

Firstly, it is assumed as a precondition that the inspection object exists within a column with a radius of R and at a distance of Lo from the radiation source 401. The distance between the radiation source 401 and the detector 402 is assumed as LD.

Assuming the size of a minimum defect to be recognized in this inspection as d, it is necessary that the angular interval alpha of the radiation detectors 414 satisfies the following formula:

$$\alpha \leq 2\tan^{-1}\left[\frac{d}{2(Lo + R)}\right] \quad (4)$$

Under the same assumption, it is necessary that delta satisfies the following formula:

$$\Delta \leq d \quad (5)$$

and it is necessary that theta satisfies the following formula:

$$\theta \geq 2\tan^{-1}\left[\frac{\Delta}{2(Lo - R)}\right] \quad (6)$$

For example, assuming Lo as 500 mm, R as 200 mm, and d as 5 mm, it is necessary that α is 0.41° or less. It is also necessary that Δ is 5 mm or less. When Δ is set to 4 mm, it is necessary that theta is 0.76° or more.

In this example, the minimum discrimination size of a defect is specified and the apparatus parameters α, Δ, and θ are set. However, when the apparatus parameters are set inversely, the minimum discrimination size of a defect is determined. For example, assuming that Lo and R are the same values as those indicated above, and α is 1.0°, and θ is 1.0°, it is necessary that Δ is 5.24 mm or more. When Δ is set to 6.0 mm, 12.2 mm which is the larger numeral among the values of d determined by a numeral 4 and a numeral 5 is the minimum discrimination size of a defect. Therefore, the interval alpha of the radiation detectors 414 arranged in the one-dimensional array of detectors 413 is determined on the basis of the necessary minimum discrimination size. The number of radiation detectors 414 is determined on the basis of the size of the inspection object area.

According to this embodiment, the position of a defect existing in an inspection object can be specified at high speed.

What is claimed is:

1. A two-dimensional radiation detection device comprising:
    a plurality of radiation detectors including collimators arranged two-dimensionally in a unitary body each including a collimator, a plastic scintillation fiber and a connector connecting the plastic scintillation fiber with a transmission optical fiber, a photoelectric conversion element to which a respective transmission optical fiber is connected and a driver for moving said radiation detectors in the unitary body two-dimensionally over a plane where said radiation detectors are arranged, said driver moving said radiation detectors in the unitary body by a fraction of a spacing distance defined by neighboring radiation detectors at one time so as to interpolate previous radiation detections by respective radiation detectors.

2. A method of non-destructive inspection of an inspection object with a non-destructive inspection apparatus comprising a radiation source for generating a radiation beam to be irradiated onto an inspection object, and a radiation detector for detecting a radiation beam transmitted through the inspection object for inspecting the inside structure of the inspection object, wherein said radiation detector is constituted by a one-dimensional array of detector units movable at least between a first position and a second position in a vertical direction, each of the first and second positions being located substantially equidistant from said radiation source and spaced apart by an angle $\theta$ in the vertical direction, and the detector units being spaced apart from one another by an angle $\alpha$ in an arrangement direction of the detector units, and said radiation source and said radiation detector are supported to move in the vertical direction which is perpendicular to the arrangement direction of the one-dimensional array of detector units with the mutual relative position therebetween kept unchanged so that by relative movement of said radiation source and said radiation detector with respect to the inspection object a first transmission image of the inspection object is obtained via the one dimensional array at the first position and a second transmission image of the inspection object is obtained via the one dimensional array at the second position, comprising the steps of:
    displaying the first transmission image obtained via the one-dimensional array at the first position and the second transmission image obtained via the one-dimensional array at a second position on a display;
    designating an area in the first transmission image as a possible defect;
    searching an area in the second transmission image having the highest correlation coefficient with the designated area of a possible defect in the first transmission image to determine a movement distance D from the possible defect area in the first transmission image to the area in the second transmission image having the highest correlation coefficient; and
    calculating the position of defect in the inspection object based on the determined movement amount D, the predetermined angles $\theta$ and $\alpha$, a predetermined sampling interval $\Delta$, a sampling start position SS and coordinate positions X1, Y1, X2, Y2 of the designated possible defect area.

3. A non-destructive inspection apparatus comprising a radiation source for generating a radiation beam to be irradiated onto an inspection object, and a radiation detector for detecting the radiation beam transmitted through the inspection object for inspecting the inside structure of the inspection object, wherein said radiation detector is constituted by a two layers of one-dimensional arrays of a plurality of detector units, including an upper layer one dimensional array of plural detector units and a lower layer one-dimensional array of plural detector units, the upper layer and the lower layer being arranged substantially equi-distant from said radiation source and spaced apart by an angle $\theta$ in the layer direction thereof, and the plurality of detector units in the upper and lower layer one-dimensional arrays being spaced apart from one another by an angle $\alpha$ in the arrangement direction thereof, and wherein said radiation source and said radiation detector are supported to move perpendicularly to the arrangement direction of the respective upper and lower layer one-dimensional arrays with the mutual relative position therebetween kept unchanged so that by relative movement of said radiation source and said radiation detector with respect to the inspection object, a first transmission image of the inspection object is obtained via the upper layer one dimensional array and a second transmission image of the inspection object is obtained via the lower layer one dimensional array.

4. A method of non-destructive inspection of an inspection object with the non-destructive inspection apparatus according to claim 3, comprising the steps of:
    displaying the first transmission image obtained via the upper layer one-dimensional array and the second transmission image obtained via the lower layer one-dimensional array on a display;
    designating an area in the first transmission image as a possible defect;
    searching an area in the second transmission image having the highest correlation coefficient with the designated area of a possible defect in the first transmission image to determine a movement distance D from the possible defect area in the first transmission image to the area in the second transmission image having the highest correlation coefficient; and
    calculating the position of defect in the inspection object based on the determined movement amount D, the predetermined angles $\theta$ and $\alpha$, a predetermined sampling interval $\Delta$, a sampling start position SS and coordinate positions X1, Y1, X2, Y2 of the designated possible defect area.

* * * * *